US010463866B2

(12) United States Patent
Stahmann et al.

(10) Patent No.: US 10,463,866 B2
(45) Date of Patent: Nov. 5, 2019

(54) SYSTEMS AND METHODS FOR TREATING CARDIAC ARRHYTHMIAS

(71) Applicant: CARDIAC PACEMAKERS, INC., St. Paul, MN (US)

(72) Inventors: Jeffrey E. Stahmann, Ramsey, MN (US); Michael J. Kane, Roseville, MN (US); William J. Linder, Golden Valley, MN (US); Howard D. Simms, Jr., Shoreview, MN (US); Keith R. Maile, New Brighton, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 492 days.

(21) Appl. No.: 14/793,325

(22) Filed: Jul. 7, 2015

(65) Prior Publication Data

US 2016/0008615 A1    Jan. 14, 2016

Related U.S. Application Data

(60) Provisional application No. 62/023,601, filed on Jul. 11, 2014.

(51) Int. Cl.
*A61N 1/36*    (2006.01)
*A61N 1/39*    (2006.01)
(Continued)

(52) U.S. Cl.
CPC ........... *A61N 1/3962* (2013.01); *A61N 1/365* (2013.01); *A61N 1/3621* (2013.01);
(Continued)

(58) Field of Classification Search
None
See application file for complete search history.

(56) References Cited

U.S. PATENT DOCUMENTS 4,333,470 A    6/1982 Barthel
4,531,527 A    7/1985 Reinhold, Jr. et al.
(Continued)

FOREIGN PATENT DOCUMENTS

CN    101102811    1/2008
CN    102458572    12/2014
(Continued)

OTHER PUBLICATIONS

Duru et al., "The Potential for Inappropriate Ventricular Tachycardia Confirmation Using the Intracardiac Electrogram (EGM) Width Criterion", Pacing and Clinical Electrophysiology [PACE], 22(7): 1039-1046, Jul. 1999.

(Continued)

*Primary Examiner* — Ankit D Tejani
(74) *Attorney, Agent, or Firm* — Seager, Tufte & Wickhem LLP.

(57) ABSTRACT

Systems and methods for treating cardiac arrhythmias. One example medical device system for delivering electrical stimulation therapy to a heart of a patient may comprise a leadless cardiac pacemaker (LCP) implanted within a heart of a patient and configured to determine occurrences of cardiac arrhythmias, a medical device configured to determine occurrences of cardiac arrhythmias and to deliver defibrillation shock therapy to the patient, wherein the LCP and the medical device are spaced from one another and communicatively coupled, and wherein after the LCP determines an occurrence of a cardiac arrhythmia, the LCP is configured to modify the defibrillation shock therapy of the medical device.

20 Claims, 13 Drawing Sheets

(51) Int. Cl.
  *A61N 1/362* (2006.01)
  *A61N 1/365* (2006.01)
  *A61N 1/372* (2006.01)
  *A61N 1/375* (2006.01)
(52) U.S. Cl.
  CPC ....... *A61N 1/3756* (2013.01); *A61N 1/37205* (2013.01); *A61N 1/37288* (2013.01); *A61N 1/3925* (2013.01); *A61N 1/3987* (2013.01)

(56) References Cited

U.S. PATENT DOCUMENTS

| | | |
|---|---|---|
| 4,539,999 A | 9/1985 | Mans |
| 4,562,841 A | 1/1986 | Brockway et al. |
| 4,585,004 A | 4/1986 | Brownlee |
| 4,589,420 A | 5/1986 | Adams et al. |
| RE32,378 E | 3/1987 | Barthel |
| 4,787,389 A | 11/1988 | Tarjan |
| 4,884,345 A | 12/1989 | Long |
| 4,924,875 A | 5/1990 | Chamoun |
| 5,000,189 A | 3/1991 | Throne et al. |
| 5,002,052 A | 3/1991 | Haluska |
| 5,014,698 A | 5/1991 | Cohen |
| 5,107,850 A | 4/1992 | Olive |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevoius et al. |
| 5,139,028 A | 8/1992 | Steinhaus et al. |
| 5,156,148 A | 10/1992 | Cohen |
| 5,161,527 A | 11/1992 | Nappholz et al. |
| 5,193,550 A | 3/1993 | Duffin |
| 5,205,283 A | 4/1993 | Olson |
| 5,215,098 A | 6/1993 | Steinhaus et al. |
| 5,217,021 A | 6/1993 | Steinhaus et al. |
| 5,255,186 A | 10/1993 | Steinhaus et al. |
| 5,265,602 A | 11/1993 | Anderson et al. |
| 5,271,411 A | 12/1993 | Ripley et al. |
| 5,273,049 A | 12/1993 | Steinhaus et al. |
| 5,275,621 A | 1/1994 | Mehra |
| 5,292,348 A | 3/1994 | Saumarez et al. |
| 5,312,445 A | 5/1994 | Nappholz et al. |
| 5,313,953 A | 5/1994 | Yomtov et al. |
| 5,324,310 A | 6/1994 | Greeninger et al. |
| 5,331,966 A | 7/1994 | Bennett et al. |
| 5,360,436 A | 11/1994 | Alt et al. |
| 5,366,487 A | 11/1994 | Adams et al. |
| 5,378,775 A | 1/1995 | Shimizu et al. |
| 5,379,775 A | 1/1995 | Kruse |
| 5,379,776 A | 1/1995 | Murphy et al. |
| 5,388,578 A | 2/1995 | Yomtov et al. |
| 5,400,795 A | 3/1995 | Murphy et al. |
| 5,411,031 A | 5/1995 | Yomtov |
| 5,447,524 A | 9/1995 | Alt |
| 5,448,997 A | 9/1995 | Kruse et al. |
| 5,456,261 A | 10/1995 | Luczyk |
| 5,458,623 A | 10/1995 | Lu et al. |
| 5,503,160 A | 4/1996 | Pering et al. |
| 5,509,927 A | 4/1996 | Epstein et al. |
| 5,520,191 A | 5/1996 | Karlsson et al. |
| 5,531,767 A | 7/1996 | Fain |
| 5,545,186 A | 8/1996 | Olson et al. |
| 5,620,471 A | 4/1997 | Duncan |
| 5,630,425 A | 5/1997 | Panescu et al. |
| 5,634,468 A | 6/1997 | Platt et al. |
| 5,645,070 A | 7/1997 | Turcott |
| 5,682,900 A | 11/1997 | Arand et al. |
| 5,683,425 A | 11/1997 | Hauptmann |
| 5,712,801 A | 1/1998 | Turcott |
| 5,713,367 A | 2/1998 | Arnold et al. |
| 5,738,105 A | 4/1998 | Kroll |
| 5,741,312 A | 4/1998 | Vonk et al. |
| 5,755,736 A | 5/1998 | Gillberg et al. |
| 5,766,225 A | 6/1998 | Kramm |
| 5,772,692 A | 6/1998 | Armstrong |
| 5,776,168 A | 7/1998 | Gunderson |
| 5,779,645 A | 7/1998 | Olson et al. |
| 5,792,065 A | 8/1998 | Xue et al. |
| 5,795,303 A | 8/1998 | Swanson et al. |
| 5,817,133 A | 10/1998 | Houben |
| 5,819,741 A | 10/1998 | Karlsson et al. |
| 5,827,197 A | 10/1998 | Bocek et al. |
| 5,848,972 A | 12/1998 | Triedman et al. |
| 5,857,977 A | 1/1999 | Caswell et al. |
| 5,873,897 A | 2/1999 | Armstrong et al. |
| 5,891,170 A | 4/1999 | Nitzsche et al. |
| 5,935,081 A | 8/1999 | Kadhiresan |
| 5,954,662 A | 9/1999 | Swanson et al. |
| 5,978,707 A | 11/1999 | Krig et al. |
| 6,108,578 A | 8/2000 | Bardy et al. |
| 6,151,524 A | 11/2000 | Krig et al. |
| 6,169,918 B1 | 1/2001 | Haefner et al. |
| 6,178,350 B1 | 1/2001 | Olson et al. |
| 6,179,865 B1 | 1/2001 | Hsu et al. |
| 6,212,428 B1 | 4/2001 | Hsu et al. |
| 6,223,078 B1 | 4/2001 | Marcovecchio |
| 6,230,055 B1 | 5/2001 | Sun et al. |
| 6,230,059 B1 | 5/2001 | Duffin |
| 6,266,554 B1 | 7/2001 | Hsu et al. |
| 6,275,732 B1 | 8/2001 | Hsu et al. |
| 6,308,095 B1 | 10/2001 | Hsu et al. |
| 6,312,388 B1 | 11/2001 | Marcovecchio et al. |
| 6,317,632 B1 | 11/2001 | Krig et al. |
| 6,405,083 B1 | 6/2002 | Rockwell et al. |
| 6,421,563 B1 | 7/2002 | Sullivan et al. |
| 6,430,435 B1 | 8/2002 | Hsu et al. |
| 6,434,417 B1 | 8/2002 | Lovett |
| 6,449,503 B1 | 9/2002 | Hsu |
| 6,456,871 B1 | 9/2002 | Hsu et al. |
| 6,477,404 B1 | 11/2002 | Yonce et al. |
| 6,480,733 B1 | 11/2002 | Turcott |
| 6,484,055 B1 | 11/2002 | Marcovecchio |
| 6,493,579 B1 | 12/2002 | Gilkerson et al. |
| 6,505,067 B1 | 1/2003 | Lee et al. |
| 6,512,940 B1 | 1/2003 | Brabec et al. |
| 6,522,915 B1 | 2/2003 | Ceballos et al. |
| 6,522,917 B1 | 2/2003 | Hsu et al. |
| 6,522,925 B1 | 2/2003 | Gilkerson et al. |
| 6,526,313 B2 | 2/2003 | Sweeney et al. |
| 6,584,352 B2 | 6/2003 | Combs et al. |
| 6,618,619 B1 | 9/2003 | Florio et al. |
| 6,622,046 B2 | 9/2003 | Fraley et al. |
| 6,658,283 B1 | 12/2003 | Bomzin et al. |
| 6,658,286 B2 | 12/2003 | Seim |
| 6,671,548 B1 | 12/2003 | Mouchawar et al. |
| 6,687,540 B2 | 2/2004 | Marcovecchio |
| 6,708,058 B2 | 3/2004 | Kim et al. |
| 6,718,204 B2 | 4/2004 | DeGroot et al. |
| 6,728,572 B2 | 4/2004 | Hsu et al. |
| 6,745,068 B2 | 6/2004 | Koyrakh et al. |
| 6,760,615 B2 | 7/2004 | Ferek-Petric |
| 6,766,190 B2 | 7/2004 | Ferek-Petric |
| 6,889,081 B2 | 5/2005 | Hsu |
| 6,892,094 B2 | 5/2005 | Ousdigian et al. |
| 6,959,212 B2 | 10/2005 | Hsu et al. |
| 6,978,177 B1 | 12/2005 | Chen et al. |
| 7,031,764 B2 | 4/2006 | Schwartz et al. |
| 7,039,463 B2 | 5/2006 | Marcovecchio |
| 7,162,298 B2 | 1/2007 | Ideker et al. |
| 7,203,535 B1 | 4/2007 | Hsu et al. |
| 7,228,176 B2 | 6/2007 | Smith et al. |
| 7,260,433 B1 | 8/2007 | Falkenberg et al. |
| 7,515,956 B2 | 4/2009 | Thompson |
| 7,565,195 B1 | 7/2009 | Kroll et al. |
| 7,751,890 B2 | 7/2010 | McCabe et al. |
| 7,761,150 B2 | 7/2010 | Ghanem et al. |
| 7,937,135 B2 | 5/2011 | Ghanem et al. |
| 7,991,471 B2 | 8/2011 | Ghanem et al. |
| 7,996,087 B2 | 8/2011 | Cowan et al. |
| 8,131,360 B2 | 3/2012 | Perschbacher et al. |
| 8,170,663 B2 | 5/2012 | DeGroot et al. |
| 8,352,025 B2 | 1/2013 | Jacobson |
| 8,386,051 B2 | 2/2013 | Rys |
| 8,457,742 B2 | 6/2013 | Jacobson |

(56) References Cited

U.S. PATENT DOCUMENTS

| | | |
|---|---|---|
| 8,478,399 B2 | 7/2013 | Degroot et al. |
| 8,571,678 B2 | 10/2013 | Wang |
| 8,744,572 B1 | 6/2014 | Greenhut et al. |
| 8,923,963 B2 | 12/2014 | Bonner et al. |
| 2002/0002389 A1 | 1/2002 | Bradley et al. |
| 2002/0032469 A1 | 3/2002 | Marcovecchio |
| 2002/0035335 A1 | 3/2002 | Schauerte |
| 2002/0049474 A1 | 4/2002 | Marcovecchio et al. |
| 2002/0072778 A1 | 6/2002 | Guck et al. |
| 2002/0087091 A1 | 7/2002 | Koyrakh et al. |
| 2002/0091333 A1 | 7/2002 | Hsu et al. |
| 2002/0107552 A1 | 8/2002 | Krig et al. |
| 2002/0123768 A1 | 9/2002 | Gilkerson et al. |
| 2002/0123769 A1 | 9/2002 | Panken et al. |
| 2002/0123770 A1 | 9/2002 | Combs et al. |
| 2002/0143370 A1 | 10/2002 | Kim |
| 2002/0147407 A1 | 10/2002 | Seim |
| 2002/0147474 A1 | 10/2002 | Seim et al. |
| 2002/0183637 A1 | 12/2002 | Kim et al. |
| 2002/0183639 A1 | 12/2002 | Sweeney et al. |
| 2002/0198461 A1 | 12/2002 | Hsu et al. |
| 2003/0004552 A1 | 1/2003 | Plombon et al. |
| 2003/0050563 A1 | 3/2003 | Suribhotla et al. |
| 2003/0060849 A1 | 3/2003 | Hsu |
| 2003/0069609 A1 | 4/2003 | Thompson |
| 2003/0083586 A1 | 5/2003 | Ferek-Petric |
| 2003/0083587 A1 | 5/2003 | Ferek-Petric |
| 2003/0083703 A1 | 5/2003 | Zhu et al. |
| 2003/0100923 A1 | 5/2003 | Bjorling et al. |
| 2003/0105491 A1 | 6/2003 | Gilkerson et al. |
| 2003/0109792 A1 | 6/2003 | Hsu et al. |
| 2003/0114889 A1 | 6/2003 | Huvelle et al. |
| 2003/0120316 A1 | 6/2003 | Spinelli et al. |
| 2003/0181818 A1 | 9/2003 | Kim et al. |
| 2003/0208238 A1 | 11/2003 | Weinberg et al. |
| 2004/0015090 A1 | 1/2004 | Sweeney et al. |
| 2004/0077995 A1 | 4/2004 | Ferek-Petric et al. |
| 2004/0093035 A1 | 5/2004 | Schwartz et al. |
| 2004/0116820 A1 | 6/2004 | Daum et al. |
| 2004/0116972 A1 | 6/2004 | Marcovecchio |
| 2004/0127806 A1 | 7/2004 | Sweeney et al. |
| 2004/0176694 A1 | 9/2004 | Kim et al. |
| 2005/0010257 A1 | 1/2005 | Lincoln et al. |
| 2005/0149134 A1 | 7/2005 | McCabe et al. |
| 2005/0149135 A1 | 7/2005 | Krig et al. |
| 2005/0159781 A1 | 7/2005 | Hsu |
| 2005/0197674 A1 | 9/2005 | McCabe et al. |
| 2005/0256544 A1 | 11/2005 | Thompson |
| 2006/0009831 A1 | 1/2006 | Lau et al. |
| 2006/0015148 A1 | 1/2006 | McCabe et al. |
| 2006/0074330 A1 | 4/2006 | Smith et al. |
| 2006/0122527 A1 | 6/2006 | Marcovecchio |
| 2006/0173498 A1 | 8/2006 | Banville et al. |
| 2006/0241701 A1 | 10/2006 | Markowitz et al. |
| 2006/0265018 A1 | 11/2006 | Smith et al. |
| 2006/0281998 A1 | 12/2006 | Li |
| 2007/0088394 A1 | 4/2007 | Jacobson |
| 2007/0088397 A1 | 4/2007 | Jacobson |
| 2007/0088398 A1 | 4/2007 | Jacobson |
| 2008/0045850 A1 | 2/2008 | Phillips |
| 2009/0171408 A1 | 7/2009 | Solem |
| 2010/0069986 A1 | 3/2010 | Stahl et al. |
| 2010/0118798 A1 | 5/2010 | Chun et al. |
| 2010/0228308 A1 | 9/2010 | Cowan et al. |
| 2011/0071586 A1 | 3/2011 | Jacobson |
| 2011/0190835 A1 | 8/2011 | Brockway et al. |
| 2012/0109235 A1 | 5/2012 | Jacobson |
| 2012/0109236 A1 | 5/2012 | Jacobsen et al. |
| 2012/0172941 A1 | 7/2012 | Rys |
| 2012/0316613 A1 | 12/2012 | Keefe et al. |
| 2013/0066169 A1 | 3/2013 | Rys et al. |
| 2013/0231710 A1 | 9/2013 | Jacobson |
| 2014/0039570 A1 | 2/2014 | Carroll et al. |
| 2014/0121719 A1 | 5/2014 | Bonner et al. |
| 2014/0121720 A1 | 5/2014 | Bonner et al. |
| 2014/0214104 A1 | 7/2014 | Greenhut et al. |

FOREIGN PATENT DOCUMENTS

| | | |
|---|---|---|
| EP | 0253505 A2 | 1/1988 |
| EP | 0308536 A1 | 3/1989 |
| EP | 0360412 A1 | 3/1990 |
| EP | 0401962 A2 | 12/1990 |
| EP | 0469817 A2 | 2/1992 |
| EP | 0506230 A1 | 9/1992 |
| EP | 0554208 A2 | 8/1993 |
| EP | 0597459 A2 | 5/1994 |
| EP | 0617980 A2 | 10/1994 |
| EP | 0711531 A1 | 5/1996 |
| EP | 0744190 A2 | 11/1996 |
| EP | 0748638 A2 | 12/1996 |
| EP | 0784996 A1 | 7/1997 |
| EP | 0848965 A2 | 6/1998 |
| EP | 0879621 A2 | 11/1998 |
| EP | 0919256 A1 | 6/1999 |
| EP | 0993842 A1 | 4/2000 |
| EP | 1112756 A2 | 7/2001 |
| WO | 9302746 A1 | 2/1993 |
| WO | 9401173 A1 | 1/1994 |
| WO | 9739681 A1 | 10/1997 |
| WO | 9739799 A1 | 10/1997 |
| WO | 9825669 A1 | 6/1998 |
| WO | 9840010 A1 | 9/1998 |
| WO | 9848891 A1 | 11/1998 |
| WO | 9853879 A1 | 12/1998 |
| WO | 9915232 A1 | 4/1999 |
| WO | 0053089 A1 | 9/2000 |
| WO | 0059573 A1 | 10/2000 |
| WO | 0113993 A1 | 3/2001 |
| WO | 0126733 A1 | 4/2001 |
| WO | WO2011063848 A1 | 6/2001 |
| WO | 03047690 A2 | 6/2003 |
| WO | 2005089643 A1 | 9/2005 |
| WO | 2006020198 A2 | 2/2006 |
| WO | 2006020198 A3 | 5/2006 |
| WO | 2006049767 A1 | 5/2006 |
| WO | WO2007033226 A2 | 3/2007 |

OTHER PUBLICATIONS

Hughes et al., "The Effects of Electrode Position on the Detection of the Transvenous Cardiac Electrogram", PACE, 3(6): 651-655, Nov. 1980.

International Search Report and Written Opinion for Application No. PCT/US2005/035057, 17 pages, dated Feb. 1, 2006.

Kinoshita et al., "Letter to the Editor", Journal of Electrocardiology, 29(3): 255-256, Jul. 1996.

Leitch et al., "Feasibility of an Implantable Arrhythmia Monitor", PACE, 15(12): 2232-2235, Dec. 1992.

Mazur et al., "Functional Similarity Between Electrograms Recorded from an Implantable Cardioverter Defibrillator Emulator and the Surface Electrocardiogram", PACE, 24(1): 34-40, Jan. 2001.

Medtronic, "Marquis™ DR 7274 Dual Chamber Implantable Cardioverter Defibrillator", Reference Manual, 426 pgs., Feb. 2002.

Morris et al., "Detection of Atrial Arrhythmia for Cardiac Rhythm Management by Implantable Devices", Journal of Electrocardiology, vol. 33, Supplement 1, pp. 133-139, 2000.

Theres et al., "Electrogram Signals Recorded from Acute and Chronic Pacemaker Implantation Sites in Pacemaker Patients", PACE, 21(1): 11-17, Jan. 1998.

SYSTEMS AND METHODS FOR TREATING CARDIAC ARRHYTHMIAS

CROSS-REFERENCE TO RELATED APPLICATIONS

This application claims priority under 35 U.S.C. § 119 to U.S. Provisional Application Ser. No. 62/023,601, filed Jul. 11, 2014, the entirety of which is incorporated herein by reference.

TECHNICAL FIELD

The present disclosure generally relates to systems, devices, and methods for treating cardiac arrhythmias, and more particularly, to systems, devices, and methods for detecting cardiac arrhythmias and coordinating therapy between multiple devices.

BACKGROUND

Pacing instruments can be used to treat patients suffering from various heart conditions that may result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) can be implanted in a patient's body. Such devices may monitor and provide electrical stimulation to the heart to help the heart operate in a more normal, efficient and/or safe manner. In some cases, a patient may have multiple implanted devices.

SUMMARY

The present disclosure generally relates to systems, devices, and methods for treating cardiac arrhythmias, and more particularly, to systems, devices, and methods for detecting cardiac arrhythmias and coordinating treatment of anti-tachycardia pacing (ATP) therapy and defibrillation shock therapy between a leadless cardiac pacemaker and another medical device.

In a first example, a medical device system for delivering electrical stimulation therapy to a heart of a patient may comprise: a leadless cardiac pacemaker (LCP) configured to be implanted within a heart of a patient and configured to determine occurrences of cardiac arrhythmias; a medical device configured to determine occurrences of cardiac arrhythmias and to deliver defibrillation shock therapy to the patient, wherein the LCP and the medical device are housed separately from one another and communicatively coupled, and wherein after the LCP determines an occurrence of a cardiac arrhythmia, the LCP is configured to modify the defibrillation shock therapy of the medical device.

Additionally or alternatively, in any of the previous examples, the LCP may determine an occurrence of a cardiac arrhythmia based, at least in part, on one or more received physiological signals or indications of one or more physiological conditions of the patient.

Additionally or alternatively, in any of the previous examples, the one or more received physiological signals may comprise one or more of: cardiac electrical activity; contractility of the heart of the patient; cardiac output of the heart of the patient; and hearts sounds.

Additionally or alternatively, in any of the previous examples, the defibrillation shock therapy may comprise, after the medical device determines an occurrence of a cardiac arrhythmia: charging a capacitor to a predefined level; and after charging the capacitor to the predefined level, delivering one or more defibrillation pulses to the heart of the patient using at least some energy stored in the capacitor.

Additionally or alternatively, in any of the previous examples, to modify the shock therapy of the medical device, the LCP may be configured to: determine whether the cardiac arrhythmia is susceptible to ATP therapy; and if it is determined that the cardiac arrhythmia is susceptible to ATP therapy, communicate a suspend message to the medical device and deliver anti-tachycardia pacing (ATP) therapy to the heart of the patient.

Additionally or alternatively, in any of the previous examples, to modify the defibrillation shock therapy of the medical device, the LCP may be configured to affect one or more of the following: modification of an amplitude of the one or more defibrillation pulses; modification of a timing of delivery of the one or more defibrillation pulses; and cessation of delivery of the one or more defibrillation pulses.

Additionally or alternatively, in any of the previous examples, the suspend message may cause the medical device to suspend delivering one or more defibrillation pulses to the heart of the patient after charging the capacitor to the predefined level.

Additionally or alternatively, in any of the previous examples, the suspend message may cause the medical device to cease charging the capacitor.

Additionally or alternatively, in any of the previous examples, to modify the shock therapy of the medical device, the LCP may be further configured to: determine whether a delivered ATP therapy terminated the arrhythmia; if it is determined that the delivered ATP therapy terminated the arrhythmia, communicate an abort command to the medical device; if it is determined that the delivered ATP therapy failed to terminate the arrhythmia, communicate a resume command to the medical device.

Additionally or alternatively, in any of the previous examples, after receiving the resume command, the medical device may be configured to deliver one or more defibrillation pulses to the heart of the patient.

Additionally or alternatively, in any of the previous examples, to determine if the arrhythmia is susceptible to ATP therapy, the LCP may be configured to determine whether: a beat rate of the heart of the patient is less than a threshold beat rate; a regularity of a beat rhythm of the heart of the patient is greater than a threshold regularity; and/or the arrhythmia is monomorphic.

Additionally or alternatively, in any of the previous examples, the medical device may determine occurrences of cardiac arrhythmias based, at least in part, on one or more signals received from the LCP.

Additionally or alternatively, in any of the previous examples, to modify the shock therapy of the medical device, the LCP may be configured to: determine whether the cardiac arrhythmia is susceptible to ATP therapy; if it is determined that the cardiac arrhythmia is susceptible to ATP therapy, deliver ATP therapy to the heart of the patient; determine whether the delivered ATP therapy terminated the arrhythmia; if it is determined that the delivered ATP therapy terminated the arrhythmia, communicate an abort command to the medical device; and if it is determined that the delivered ATP therapy failed to terminate the arrhythmia, communicate a shock command to the medical device.

Additionally or alternatively, in any of the previous examples, the shock command may cause the medical device to deliver one or more defibrillation pulses to the heart of the patient.

Additionally or alternatively, in any of the previous examples, the medical device may be a subcutaneous implantable cardioverter-defibrillator.

In another example, a medical device system for delivering electrical stimulation therapy to a heart of a patient may comprise: a leadless cardiac pacemaker (LCP) implanted within a heart of a patient and configured to determine occurrences of cardiac arrhythmias; a medical device configured to determine occurrences of cardiac arrhythmias and to deliver defibrillation shock therapy to the patient, wherein the LCP and the medical device are spaced from one another and communicatively coupled, and wherein after the LCP determines an occurrence of a cardiac arrhythmia, the LCP is configured to modify the defibrillation shock therapy of the medical device.

Additionally or alternatively, in any of the previous examples, the LCP may determine an occurrence of a cardiac arrhythmia based, at least in part, on one or more received physiological signals or indications of one or more physiological conditions of the patient.

Additionally or alternatively, in any of the previous examples, the defibrillation shock therapy may comprise, after the medical device determines an occurrence of a cardiac arrhythmia: charging a capacitor to a predefined level; and after charging the capacitor to the predefined level, delivering one or more defibrillation pulses to the heart of the patient using at least some energy stored in the capacitor.

Additionally or alternatively, in any of the previous examples, to modify the shock therapy of the medical device, the LCP may be configured to: determine whether the cardiac arrhythmia is susceptible to ATP therapy; and if it is determined that the cardiac arrhythmia is susceptible to ATP therapy, communicate a suspend message to the medical device and deliver anti-tachycardia pacing (ATP) therapy to the heart of the patient.

Additionally or alternatively, in any of the previous examples, the suspend message may cause the medical device to suspend delivering one or more defibrillation pulses to the heart of the patient after charging the capacitor to the predefined level.

Additionally or alternatively, in any of the previous examples, the suspend message may cause the medical device to cease charging the capacitor.

Additionally or alternatively, in any of the previous examples, to modify the shock therapy of the medical device, the LCP may be further configured to: determine whether a delivered ATP therapy terminated the arrhythmia; if it is determined that the delivered ATP therapy terminated the arrhythmia, communicate an abort command to the medical device; if it is determined that the delivered ATP therapy failed to terminate the arrhythmia, communicate a resume command to the medical device.

Additionally or alternatively, in any of the previous examples, after receiving the resume command, the medical device may be configured to deliver one or more defibrillation pulses to the heart of the patient.

Additionally or alternatively, in any of the previous examples, the medical device may determine occurrences of cardiac arrhythmias based, at least in part, on one or more signals received from the LCP.

Additionally or alternatively, in any of the previous examples, to modify the shock therapy of the medical device, the LCP may be configured to: determine whether the cardiac arrhythmia is susceptible to ATP therapy; if it is determined that the cardiac arrhythmia is susceptible to ATP therapy, deliver ATP therapy to the heart of the patient; determine whether the delivered ATP therapy terminated the arrhythmia; if it is determined that the delivered ATP therapy terminated the arrhythmia, communicate an abort command to the medical device; and if it is determined that the delivered ATP therapy failed to terminate the arrhythmia, communicate a shock command to the medical device.

Additionally or alternatively, in any of the previous examples, the shock command may cause the medical device to deliver one or more defibrillation pulses to the heart of the patient.

In still another example, a method for delivering electrical stimulation therapy to a heart of a patient may comprise: determining an occurrence of an arrhythmia; after determining an occurrence of an arrhythmia: with a leadless cardiac pacemaker (LCP), determining whether the arrhythmia is susceptible to anti-tachycardia pacing (ATP) therapy; and with a medical device that is spaced from the LCP and communicatively coupled to the LCP, initiating a shock therapy program; with the LCP, if the arrhythmia is determined to be susceptible to ATP therapy, modifying the shock therapy program of the medical device.

Additionally or alternatively, in any of the previous examples, the shock therapy program may comprise delivering one or more defibrillation pulses to the heart of the patient, and modifying the shock therapy program of the medical device comprises one or more of: modifying an amplitude of the one or more defibrillation pulses; modifying a timing of delivery of the one or more defibrillation pulses; and ceasing delivery of the one or more defibrillation pulses.

Additionally or alternatively, in any of the previous examples, the LCP may determine the arrhythmia is susceptible to ATP therapy if: a beat rate of the heart of the patient is less than a threshold beat rate; a regularity of a beat rhythm of the heart of the patient is greater than a threshold regularity; and/or the arrhythmia is monomorphic.

In yet another example, a medical device system for delivering electrical stimulation therapy to a heart of a patient may comprise: a leadless cardiac pacemaker (LCP) configured to sense one or more physiological parameters of the heart of the patient; and a medical device communicatively coupled to the LCP, the medical device configured to determine an occurrence of an arrhythmia and deliver electrical shock therapy to the heart of the patient, wherein the electrical shock therapy comprises: charging a capacitor to a predetermined level, and delivering one or more electrical shocks to the heart of the patient after charging the capacitor to the predetermined level; and wherein the medical device is configured to alter the electrical shock therapy based on communications from the LCP.

Additionally or alternatively, in any of the previous examples, the LCP may be further configured to, based on the one or more sensed physiological parameters, cause the medical device to begin charging the capacitor.

Additionally or alternatively, in any of the previous examples, the one or more physiological parameters may comprise one or more of: cardiac electrical activity; contractility of the heart of the patient; cardiac output of the heart of the patient; and hearts sounds.

Additionally or alternatively, in any of the previous examples, the LCP may cause the medical device to begin charging the capacitor before the medical device determines an occurrence of an arrhythmia.

Additionally or alternatively, in any of the previous examples, the LCP may be further configured to: communicate an indication of an occurrence of an arrhythmia to the medical device, wherein the medical device is further configured to determine an occurrence of an arrhythmia based, at least in part, on the received indication; and deliver ATP therapy before the medical device delivers electrical shock therapy to the heart of the patient.

Additionally or alternatively, in any of the previous examples, the LCP may be further configured to: determine whether the ATP therapy was successful in terminating the arrhythmia; and if it is determined that the ATP therapy was successful in terminating the arrhythmia, communicate an abort message to the medical device to abort the delivery of electrical shock therapy to the heart of the patient.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
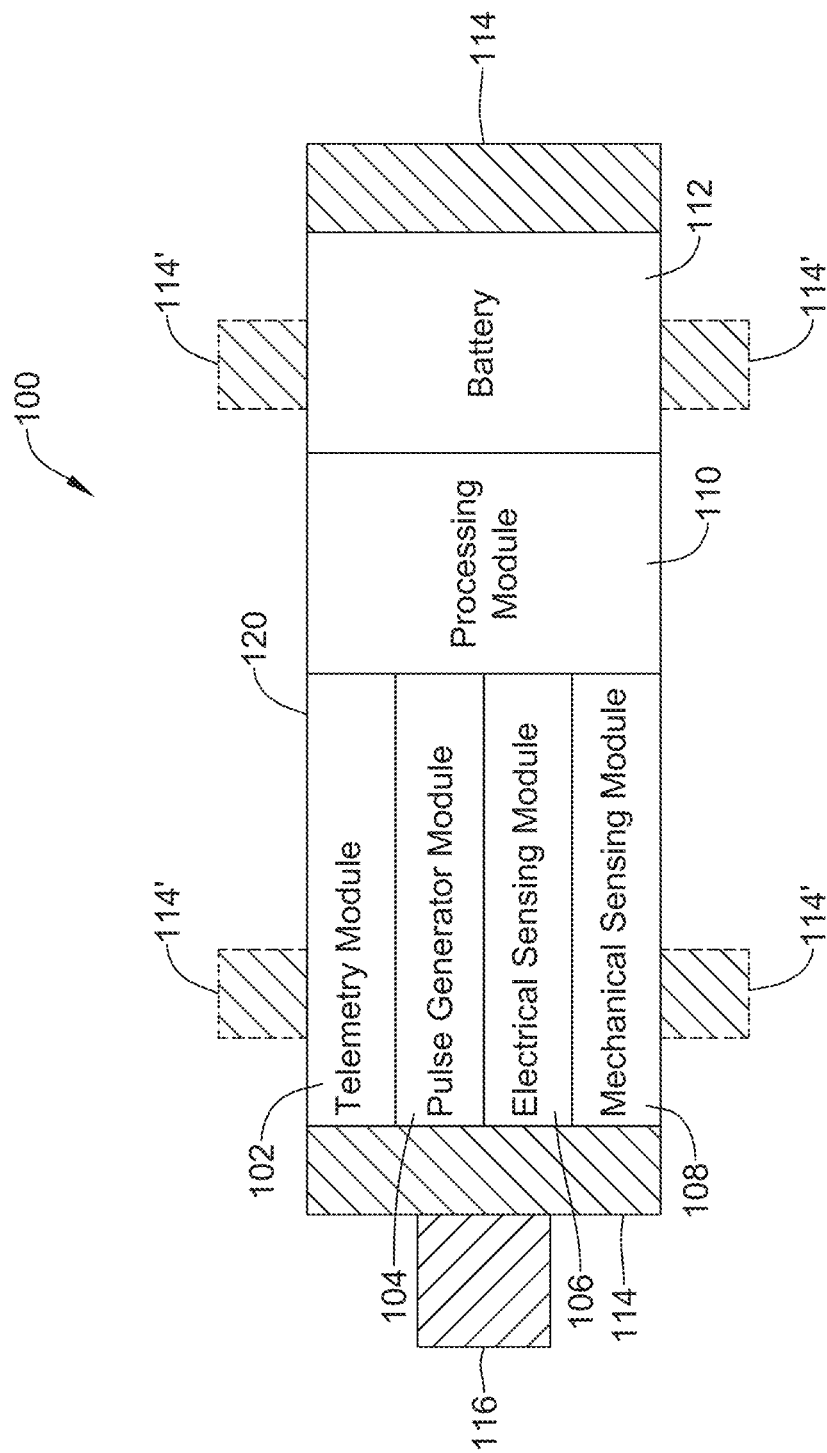
FIG. 1 is a schematic block diagram of an illustrative leadless cardiac pacemaker (LCP) according to one example of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

A normal, healthy heart induces contraction by conducting intrinsically generated electrical signals throughout the heart. These intrinsic signals cause the muscle cells or tissue of the heart to contract. This contraction forces blood out of and into the heart, providing circulation of the blood throughout the rest of the body. However, many patients suffer from cardiac conditions that affect this contractility of their hearts. For example, some hearts may develop diseased tissues that no longer generate or conduct intrinsic electrical signals. In some examples, diseased cardiac tissues conduct electrical signals at differing rates, thereby causing an unsynchronized and inefficient contraction of the heart. In other examples, a heart may generate intrinsic signals at such a low rate that the heart rate becomes dangerously low. In still other examples, a heart may generate electrical signals at an unusually high rate. In some cases such an abnormality can develop into a fibrillation state, where the contraction of the patient's heart chambers are almost completely de-synchronized and the heart pumps very little to no blood. Implantable medical device which may be configured to deliver one or more types of electrical stimulation therapy to patient's hearts may help to terminate or alleviate such cardiac conditions.

FIG. 1 depicts an exemplary leadless cardiac pacemaker (LCP) that may be implanted into a patient and may operate to prevent, control, or terminate cardiac arrhythmias in patients, for example by appropriately employing one or more therapies (e.g. anti-tachycardia pacing (ATP) therapy, cardiac resynchronization therapy (CRT), bradycardia therapy, defibrillation therapy, or the like). As can be seen in FIG. 1, LCP 100 may be a compact device with all components housed within LCP 100 or directly on housing 120. In the example shown in FIG. 1, LCP 100 may include a telemetry module 102, a pulse generator module 104, an electrical sensing module 106, a mechanical sensing module 108, a processing module 110, a battery 112, and electrodes 114. LCP 100 may include more or less modules, depending on the application.

Telemetry module 102 may be configured to communicate with devices such as sensors, other medical devices, and/or the like, that are located externally to LCP 100. Such devices may be located either external or internal to the patient's body. Irrespective of the location, external devices (i.e. external to the LCP 100 but not necessarily external to the patient's body) can communicate with LCP 100 via telemetry module 102 to accomplish one or more desired functions. For example, LCP 100 may communicate information, such as sensed electrical signals, data, instructions, messages, etc., to an external medical device through telemetry module 102. The external medical device may use the communicated signals, data, instructions and/or messages to perform various functions, such as determining occurrences of arrhythmias, delivering electrical stimulation therapy, storing received data, and/or performing any other suitable function. LCP 100 may additionally receive information such as signals, data, instructions and/or messages from the external medical device through telemetry module 102, and LCP 100 may use the received signals, data, instructions and/or messages to perform various functions, such as determining occurrences of arrhythmias, delivering electrical stimulation therapy, storing received data, and/or performing any other suitable function. Telemetry module 102 may be configured to use one or more methods for communicating with external devices. For example, telemetry module 102 may communicate via radiofrequency (RF) signals, inductive coupling, optical signals, acoustic signals, conducted communication signals, and/or any other signals suitable for communication.

In the example shown in FIG. 1, pulse generator module 104 may be electrically connected to electrodes 114. In some examples, LCP 100 may additionally include electrodes 114'. In such examples, pulse generator 104 may also be electrically connected to electrodes 114'. Pulse generator module 104 may be configured to generate electrical stimulation signals. For example, pulse generator module 104 may generate electrical stimulation signals by using energy stored in battery 112 within LCP 100 and deliver the generated electrical stimulation signals via electrodes 114 and/or 114'. Alternatively, or additionally, pulse generator 104 may include one or more capacitors, and pulse generator 104 may charge the one or more capacitors by drawing energy from battery 112. Pulse generator 104 may then use the energy of the one or more capacitors to deliver the generated electrical stimulation signals via electrodes 114 and/or 114'. In at least some examples, pulse generator 104 of LCP 100 may include switching circuitry to selectively connect one or more of electrodes 114 and/or 114' to pulse generator 104 in order to select which electrodes 114/114' (and/or other electrodes) pulse generator 104 delivers the electrical stimulation therapy. Pulse generator module 104 may generate electrical stimulation signals with particular features or in particular sequences in order to provide one or multiple of a number of different stimulation therapies. For example, pulse generator module 104 may be configured to generate electrical stimulation signals to provide electrical stimulation therapy to combat bradycardia, tachycardia, cardiac synchronization, bradycardia arrhythmias, tachycardia arrhythmias, fibrillation arrhythmias, cardiac synchronization arrhythmias and/or to produce any other suitable electrical stimulation therapy. Some more common electrical stimulation therapies include anti-tachycardia pacing (ATP) therapy, cardiac resynchronization therapy (CRT), and cardioversion/defibrillation therapy.

In some examples, LCP 100 may not include a pulse generator 104. For example, LCP 100 may be a diagnostic only device. In such examples, LCP 100 may not deliver electrical stimulation therapy to a patient. Rather, LCP 100 may collect data about cardiac electrical activity and/or physiological parameters of the patient and communicate such data and/or determinations to one or more other medical devices.

In some examples, LCP 100 may include an electrical sensing module 106, and in some cases, a mechanical sensing module 108. Electrical sensing module 106 may be configured to sense the cardiac electrical activity of the heart. For example, electrical sensing module 106 may be connected to electrodes 114/114', and electrical sensing module 106 may be configured to receive cardiac electrical signals conducted through electrodes 114/114'. The cardiac electrical signals may represent local information from the chamber in which LCP 100 is implanted. For instance, if LCP 100 is implanted within a ventricle of the heart, cardiac electrical signals sensed by LCP 100 through electrodes 114/114' may represent ventricular cardiac electrical signals. Mechanical sensing module 108 may include one or more sensors, such as an accelerometer, a blood pressure sensor, a heart sound sensor, a blood-oxygen sensor, and/or any other suitable sensors that are configured to measure one or more mechanical parameters of the patient. Both electrical sensing module 106 and mechanical sensing module 108 may be connected to a processing module 110, which may provide signals representative of the sensed mechanical parameters. Although described with respect to FIG. 1 as separate sensing modules, in some cases, electrical sensing module 206 and mechanical sensing module 208 may be combined into a single sensing module, as desired.

Electrodes 114/114' can be secured relative to housing 120 but exposed to the tissue and/or blood surrounding LCP 100. In some cases, electrodes 114 may be generally disposed on either end of LCP 100 and may be in electrical communication with one or more of modules 102, 104, 106, 108, and 110. Electrodes 114/114' may be supported by the housing 120, although in some examples, electrodes 114/114' may be connected to housing 120 only through short connecting wires such that electrodes 114/114' are not directly secured relative to housing 120. In examples where LCP 100 includes one or more electrodes 114', electrodes 114' may be generally disposed on the sides of LCP 100 and may increase the number of electrodes by which LCP 100 may sense cardiac electrical activity, deliver electrical stimulation and/or communicate with an external medical device. Electrodes 114/114' can be made up of one or more biocompatible conductive materials such as various metals or alloys that are known to be safe for implantation within a human body. In some instances, electrodes 114/114' connected to LCP 100 may have an insulative portion that electrically isolates electrodes 114/114' from adjacent electrodes, housing 120, and/or other parts of the LCP 100.

Processing module 110 can be configured to control the operation of LCP 100. For example, processing module 110 may be configured to receive electrical signals from electrical sensing module 106 and/or mechanical sensing module 108. Based on the received signals, processing module 110 may determine, for example, occurrences and, in some cases, types of arrhythmias. Based on any determined arrhythmias, processing module 110 may control pulse generator module 104 to generate electrical stimulation in accordance with one or more therapies to treat the determined arrhythmia(s). Processing module 110 may further receive information from telemetry module 102. In some examples, processing module 110 may use such received information to help determine whether an arrhythmia is occurring, determine a type of arrhythmia, and/or to take particular action in response to the information. Processing module 110 may additionally control telemetry module 102 to send information to other devices.

In some examples, processing module 110 may include a pre-programmed chip, such as a very-large-scale integration (VLSI) chip and/or an application specific integrated circuit (ASIC). In such embodiments, the chip may be pre-programmed with control logic in order to control the operation of LCP 100. By using a pre-programmed chip, processing module 110 may use less power than other programmable circuits (e.g. general purpose programmable microprocessors) while still being able to maintain basic functionality, thereby potentially increasing the battery life of LCP 100. In other examples, processing module 110 may include a programmable microprocessor. Such a programmable microprocessor may allow a user to modify the control logic of LCP 100 even after implantation, thereby allowing for greater flexibility of LCP 100 than when using a pre-programmed ASIC. In some examples, processing module 110 may further include a memory, and processing module 110 may store information on and read information from the memory. In other examples, LCP 100 may include a separate memory (not shown) that is in communication with processing module 110, such that processing module 110 may read and write information to and from the separate memory.

Battery 112 may provide power to the LCP 100 for its operations. In some examples, battery 112 may be a non-rechargeable lithium-based battery. In other examples, a non-rechargeable battery may be made from other suitable materials, as desired. Because LCP 100 is an implantable device, access to LCP 100 may be limited after implantation. Accordingly, it is desirable to have sufficient battery capacity to deliver therapy over a period of treatment such as days, weeks, months, years or even decades. In other examples, battery 110 may a rechargeable battery, which may help increase the useable lifespan of LCP 100. In still other examples, battery 110 may be some other type of power source, as desired.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. Anchor 116 may include any one of a number of fixation or anchoring mechanisms. For example, anchor 116 may include one or more pins, staples, threads, screws, helix, tines, and/or the like. In some examples, although not shown, anchor 116 may include threads on its external surface that may run along at least a partial length of anchor 116. The threads may provide friction between the cardiac tissue and the anchor to help fix the anchor 116 within the cardiac tissue. In other examples, anchor 116 may include other structures such as barbs, spikes, or the like to facilitate engagement with the surrounding cardiac tissue.

Figure 2:
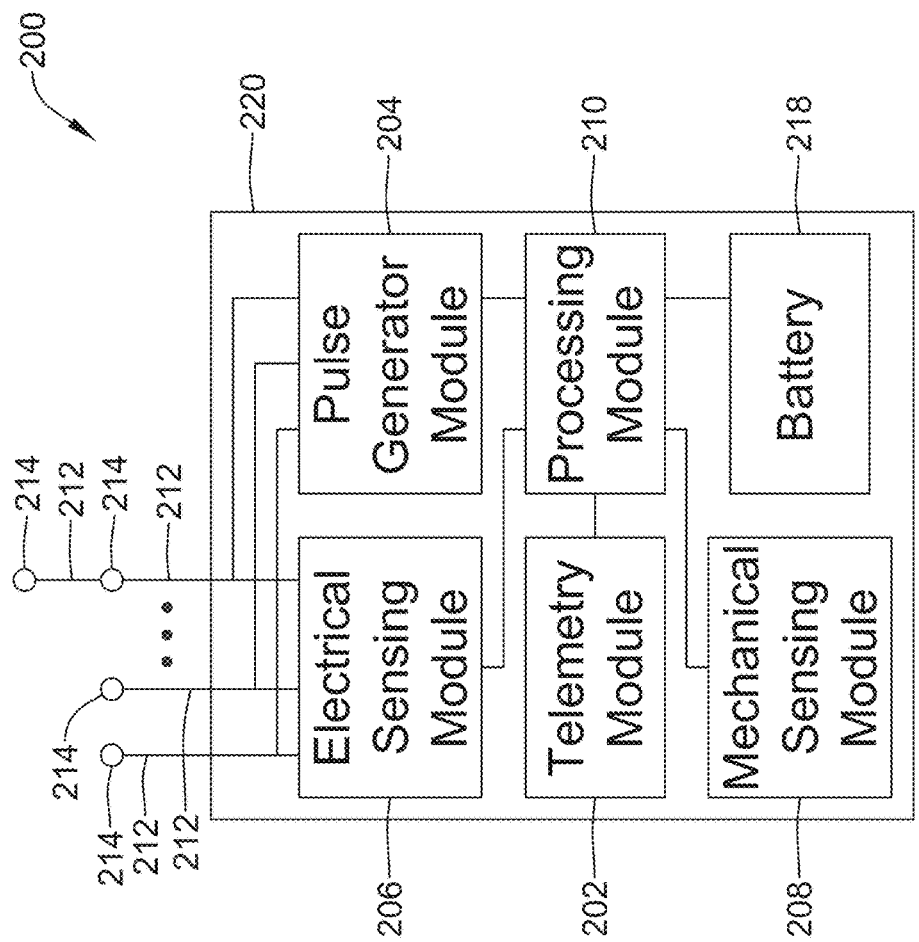
FIG. 2 is a schematic block diagram of another illustrative medical device that may be used in conjunction with the LCP of FIG. 1.

FIG. 2 depicts an example of another medical device (MD) 200, which may be used in conjunction with LCP 100 of FIG. 1 in order to detect and/or treat cardiac arrhythmias and other heart conditions. In the example shown, MD 200 may include a telemetry module 202, a pulse generator module 204, an electrical sensing module 206, a mechanical sensing module 208, a processing module 210, and a battery 218. Each of these modules may be similar to modules 102, 104, 106, 108, and 110 of LCP 100. Additionally, battery 218 may be similar to battery 112 of LCP 100. In some examples, however, MD 200 may have a larger volume within housing 220. In such examples, MD 200 may include a larger battery and/or a larger processing module 210 capable of handling more complex operations than processing module 110 of LCP 100.

While it is contemplated that MD 200 may be another leadless device such as shown in FIG. 1, in some instances MD 200 may include leads such as leads 212. Leads 212 may include electrical wires that conduct electrical signals between electrodes 214 and one or more modules located within housing 220. In some cases, leads 212 may be connected to and extend away from housing 220 of MD 200. In some examples, leads 212 are implanted on, within, or adjacent to a heart of a patient. Leads 212 may contain one or more electrodes 214 positioned at various locations on leads 212, and in some cases at various distances from housing 220. Some leads 212 may only include a single electrode 214, while other leads 212 may include multiple electrodes 214. Generally, electrodes 214 are positioned on leads 212 such that when leads 212 are implanted within the patient, one or more of the electrodes 214 are positioned to perform a desired function. In some cases, the one or more of the electrodes 214 may be in contact with the patient's cardiac tissue. In some cases, the one or more of the electrodes 214 may be positioned subcutaneously but adjacent the patient's heart. In some cases, electrodes 214 may conduct intrinsically generated electrical signals to leads 212, e.g. signals representative of intrinsic cardiac electrical activity. Leads 212 may, in turn, conduct the received electrical signals to one or more of the modules 202, 204, 206, and 208 of MD 200. In some cases, MD 200 may generate electrical stimulation signals, and leads 212 may conduct the generated electrical stimulation signals to electrodes 214. Electrodes 214 may then conduct the electrical signals and delivery the signals to the patient's heart (either directly or indirectly).

Mechanical sensing module 208, as with mechanical sensing module 108, may contain or be electrically connected to one or more sensors, such as accelerometers, blood pressure sensors, heart sound sensors, blood-oxygen sensors, and/or other sensors which are configured to measure one or more mechanical parameters of the heart and/or patient. In some examples, one or more of the sensors may be located on leads 212, but this is not required. In some examples, one or more of the sensors may be located in housing 220.

While not required, in some examples, MD 200 may be an implantable medical device. In such examples, housing 220 of MD 200 may be implanted in, for example, a transthoracic region of the patient. Housing 220 may generally include any of a number of known materials that are safe for implantation in a human body and may, when implanted, hermetically seal the various components of MD 200 from fluids and tissues of the patient's body.

In some cases, MD 200 may be an implantable cardiac pacemaker (ICP). In this example, MD 200 may have one or more leads, for example leads 212, which are implanted on or within the patient's heart. The one or more leads 212 may include one or more electrodes 214 that are in contact with cardiac tissue and/or blood of the patient's heart. MD 200 may be configured to sense intrinsically generated cardiac electrical signals and determine, for example, one or more cardiac arrhythmias based on analysis of the sensed signals. MD 200 may be configured to deliver CRT, ATP therapy, bradycardia therapy, and/or other therapy types via leads 212 implanted within the heart. In some examples, MD 200 may additionally be configured provide defibrillation therapy.

In some instances, MD 200 may be an implantable cardioverter-defibrillator (ICD). In such examples, MD 200 may include one or more leads implanted within a patient's heart. MD 200 may also be configured to sense cardiac electrical signals, determine occurrences of tachyarrhythmias based on the sensed signals, and may be configured to deliver defibrillation therapy in response to determining an occurrence of a tachyarrhythmia. In other examples, MD 200 may be a subcutaneous implantable cardioverter-defibrillator (S-ICD). In examples where MD 200 is an S-ICD, one of leads 212 may be a subcutaneously implanted lead. In at least some examples where MD 200 is an S-ICD, MD 200 may include only a single lead which is implanted subcutaneously, but this is not required.

In some examples, MD 200 may not be an implantable medical device. Rather, MD 200 may be a device external to the patient's body, and may include skin-electrodes that are placed on a patient's body. In such examples, MD 200 may be able to sense surface electrical signals (e.g. cardiac electrical signals that are generated by the heart or electrical signals generated by a device implanted within a patient's body and conducted through the body to the skin) In such examples, MD 200 may be configured to deliver various types of electrical stimulation therapy, including, for example, defibrillation therapy.

Figure 3:
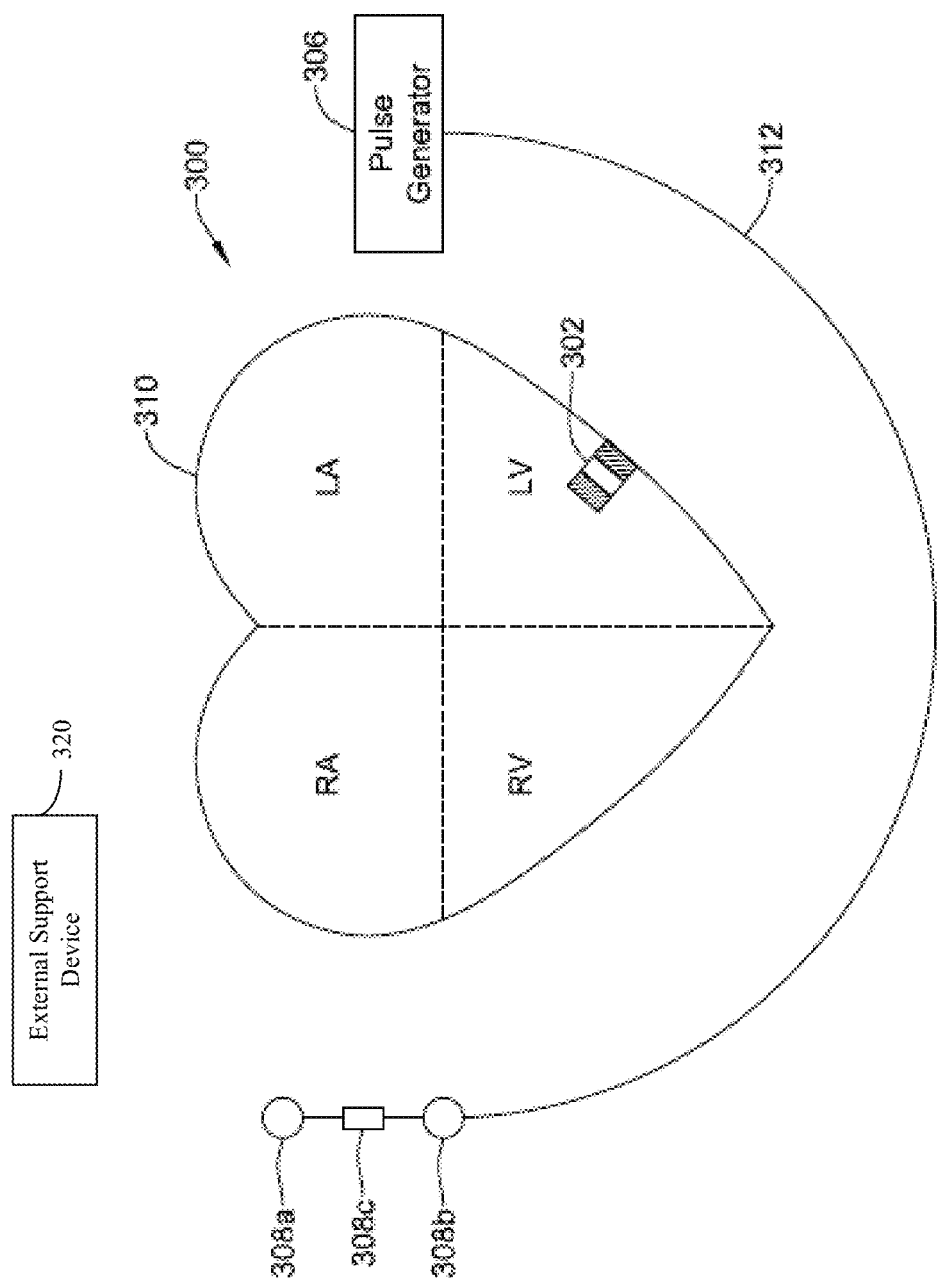
FIG. 3 is a schematic diagram of a system including a leadless cardiac pacemaker (LCP) and another medical device, in accordance with yet another example of the present disclosure.
Figure 4:
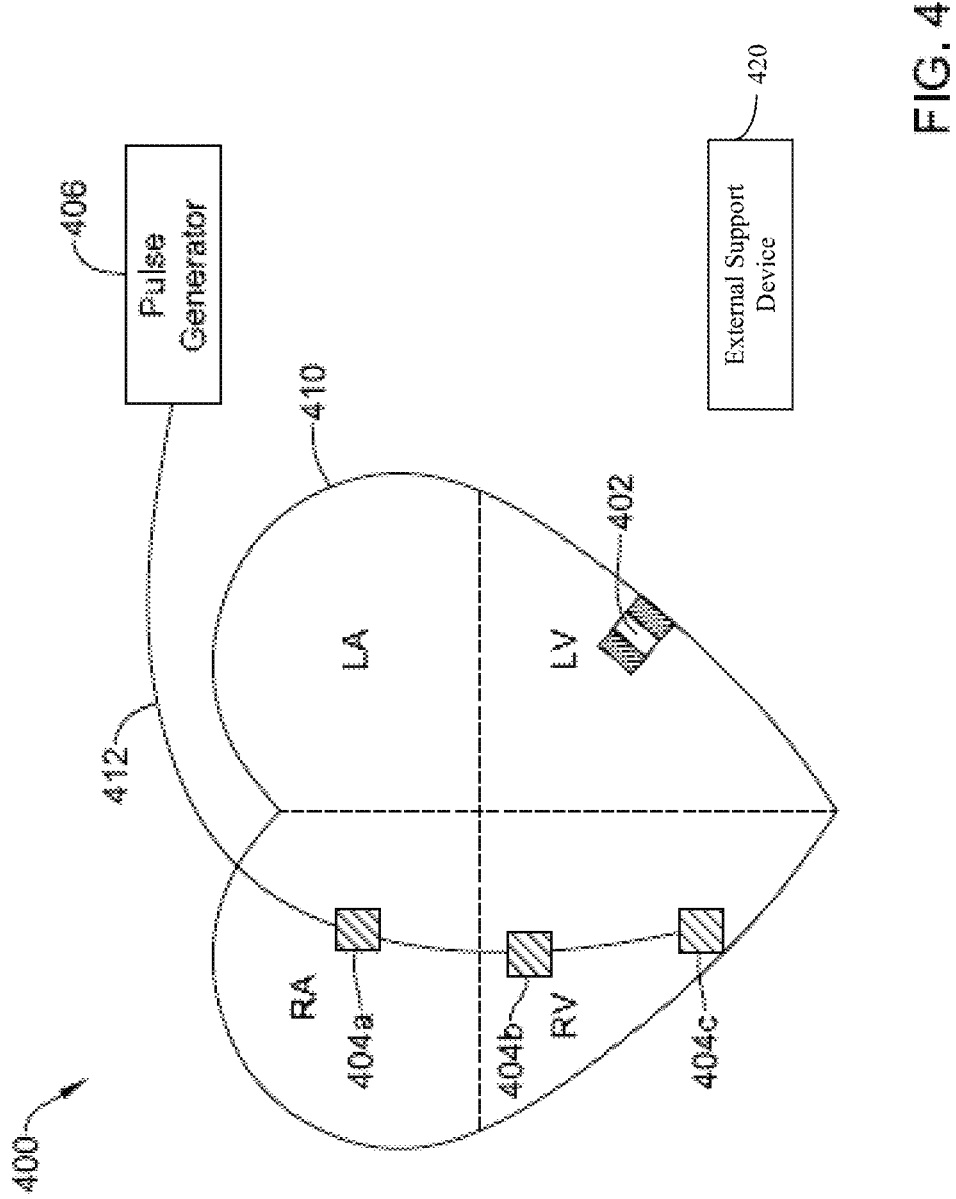
FIG. 4 is a schematic diagram of a system including an LCP and another medical device, in accordance with another example of the present disclosure.

FIGS. 3 and 4 show illustrative medical device systems that may be configured to operate according to techniques disclosed herein. In FIG. 3, an LCP 302 is shown fixed to the interior of the left ventricle of the heart 310, and a pulse generator 306 is shown coupled to a lead 312 having one or more electrodes 308*a*-308*c*. In some cases, the pulse generator 306 may be part of a subcutaneous implantable cardioverter-defibrillator (S-ICD), and the one or more electrodes 308*a*-308*c* may be positioned subcutaneously adjacent the heart. In some cases, the LCP 302 may communicate with the subcutaneous implantable cardioverter-defibrillator (S-ICD). In some cases, the LCP 302 may be in the right ventricle, right atrium or left atrium of the heart, as desired. In some cases, more than one LCP 302 may be implanted. For example, one LCP may be implanted in the right ventricle and another may be implanted in the right atrium. In another example, one LCP may be implanted in the right ventricle and another may be implanted in the left ventricle. In yet another example, one LCP may be implanted in each of the chambers of the heart.

In FIG. 4, an LCP 402 is shown fixed to the interior of the left ventricle of the heart 410, and a pulse generator 406 is shown coupled to a lead 412 having one or more electrodes 404*a*-404*c*. In some cases, the pulse generator 406 may be part of an implantable cardiac pacemaker (ICP) and/or an implantable cardioverter-defibrillator (ICD), and the one or more electrodes 404*a*-404*c* may be positioned in the heart 410. In some cases, the LCP 402 may communicate with the implantable cardiac pacemaker (ICP) and/or an implantable cardioverter-defibrillator (ICD).

The medical device systems 300 and 400 may also include an external support device, such as external support devices 320 and 420. External support devices 320 and 420 can be used to perform functions such as device identification, device programming and/or transfer of real-time and/or stored data between devices using one or more of the communication techniques described herein. As one example, communication between external support device 320 and the pulse generator 306 is performed via a wireless mode, and communication between the pulse generator 306 and LCP 302 is performed via a conducted mode. In some examples, communication between the LCP 302 and external support device 320 is accomplished by sending communication information through the pulse generator 306. However, in other examples, communication between the LCP 302 and external support device 320 may be via a telemetry module.

FIGS. 3-4 only illustrate two examples of medical device systems that may be configured to operate according to techniques disclosed herein. Other example medical device systems may include additional or different medical devices and/or configurations. For instance, other medical device systems that are suitable to operate according to techniques disclosed herein may include additional LCPs implanted within the heart. Another example medical device system may include a plurality of LCPs without other devices such as pulse generator 306 or 406, with at least one LCP capable of delivering defibrillation therapy. In yet other examples, the configuration or placement of the medical devices, leads, and/or electrodes may be different from those depicted in FIGS. 3 and 4. Accordingly, it should be recognized that numerous other medical device systems, different from those depicted in FIGS. 3 and 4, may be operated in accordance with techniques disclosed herein. As such, the examples shown in FIGS. 3 and 4 should not be viewed as limiting in any way.

Figure 5:
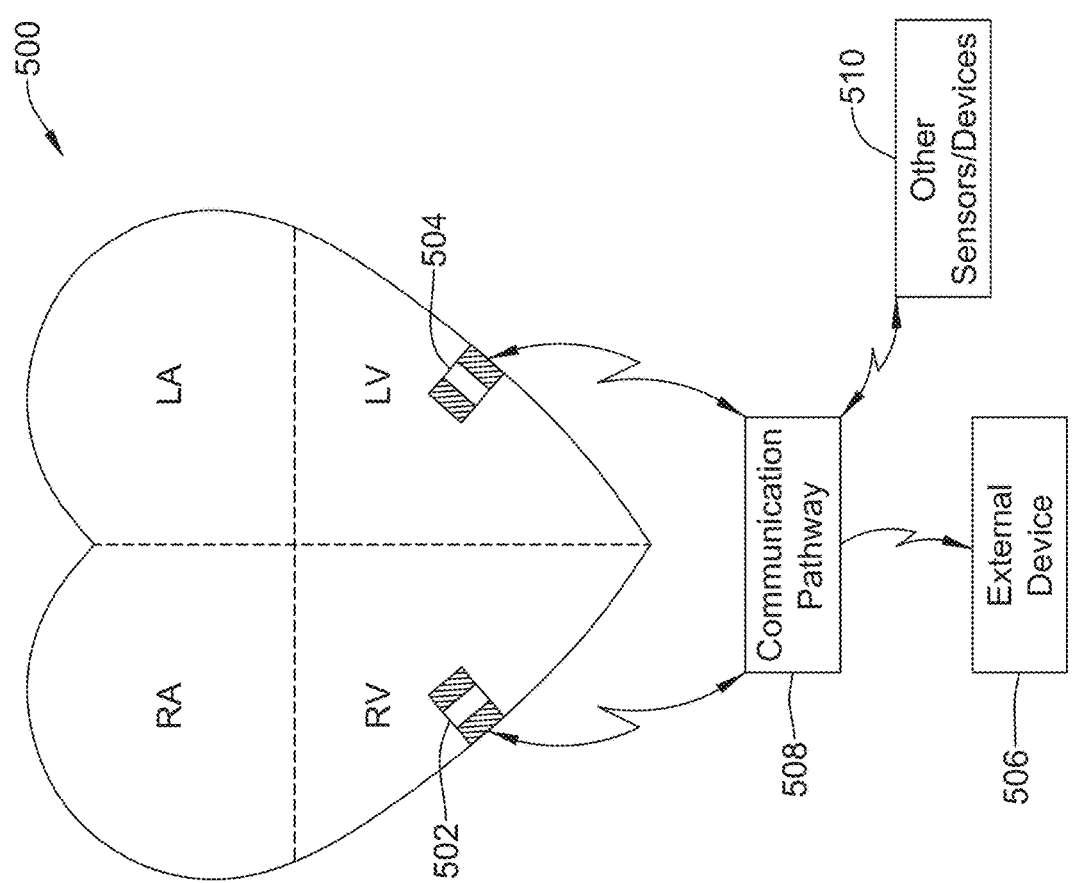
FIG. 5 is a schematic diagram of an exemplary medical system that includes multiple LCPs and/or other devices in communication with one another.

FIG. 5 illustrates an example of a medical device system and a communication pathway through which multiple medical devices 502, 504, 506 and/or 510 may communicate. In the example shown, medical device system 500 may include LCPs 502 and 504, external medical device 506, and/or other sensors/devices 510. External device 506 may be any of the devices described previously with respect to MD 200. Other sensors/devices 510 may also be any of the devices described previously with respect to MD 200. In some instances, other sensors/devices 510 may include a sensor, such as an accelerometer or blood pressure sensor, or the like. In some cases, other sensors/devices 510 may include an external programmer device that may be used to program one or more devices of system 500.

Various devices of system 500 may communicate via communication pathway 508. For example, LCPs 502 and/or 504 may sense intrinsic cardiac electrical signals and may communicate such signals to one or more other devices 502/504, 506, and 510 of system 500 via communication pathway 508. In one example, one or more of devices 502/504 may receive such signals and, based on the received signals, determine an occurrence of an arrhythmia. In some cases, device or devices 502/504 may communicate such determinations to one or more other devices 506 and 510 of system 500. In some cases, one or more of devices 502/504, 506, and 510 of system 500 may take action based on the communicated determination of an arrhythmia, such as by delivering a suitable electrical stimulation to the heart of the patient. It is contemplated that communication pathway 508 may communicate using RF signals, inductive coupling, optical signals, acoustic signals, conducted signals, or any other signals suitable for communication. Additionally, in at least some examples, device communication pathway 508 may comprise multiple signal types. For instance, other sensors/device 510 may communicate with external device 506 using a first signal type (e.g. RF communication) but communicate with LCPs 502/504 using a second signal type (e.g. conducted communication). Further, in some examples, communication between devices may be limited. For instance, in some examples, LCPs 502/504 may communicate with external device 506 only through other sensors/ devices 510, where LCPs 502/504 send signals to other sensors/devices 510, and the other sensors/devices 510 relay the received signals to external device 506.

In some cases, communication pathway 508 may include conducted communication. Accordingly, devices of system 500 may have components that allow for such conducted communication. For instance, the devices of system 500 may be configured to transmit conducted communication signals (e.g. current and/or voltage pulses) into the patient's body via one or more electrodes of a transmitting device, and may receive the conducted communication signals (e.g. pulses) via one or more electrodes of a receiving device. The patient's body may "conduct" the conducted communication signals (e.g. pulses) from the electrodes of the transmitting device to the electrodes of the receiving device. In such examples, the delivered conducted communication signals (e.g. pulses) may differ from pacing or other therapy signals. For example, the devices of system 500 may deliver electrical communication pulses at an amplitude/pulse width that is sub-threshold to the heart (e.g. non-therapeutic). Although, in some cases, the amplitude/pulse width of the delivered electrical communication pulses may be above the capture threshold of the heart, but may be delivered during a refractory period of the heart and/or may be incorporated in or modulated onto one or more pacing pulses, if desired.

Delivered electrical communication pulses may be modulated in any suitable manner to encode communicated information. In some cases, the communication pulses may be pulse width modulated or amplitude modulated. Alternatively, or in addition, the time between pulses may be modulated to encode desired information. In some cases, conducted communication pulses may be voltage pulses, current pulses, biphasic voltage pulses, biphasic current pulses, or any other suitable electrical pulse as desired.

According to some examples, a medical device system of two or more medical devices may cooperate to deliver electrical stimulation therapy to a heart of a patient. For example, a plurality of medical devices may be configured to detect cardiac arrhythmias, determine whether the arrhythmias are susceptible to a first type of electrical stimulation therapy and if it is determined that the arrhythmia is not susceptible to the first type of electrical stimulation therapy or that the first type of electrical stimulation therapy has failed, to deliver a second type of electrical stimulation therapy. Many of the examples are described in terms tachyarrhythmias, anti-tachycardia pacing (ATP) therapy, and defibrillation shock therapy. However, other types of therapy are also contemplated, including cardiac resynchronization therapy (CRT), bradycardia therapy, neuro stimulation therapy, etc. Each of the various electrical stimulation therapies may use corresponding types of electrical stimulation pulses to achieve a desired result. For instance, ATP therapy may use pacing pulses, whereas defibrillation shock therapy may use defibrillation pulses. In general, the medical devices may use any type of electrical stimulation pulses known in the art to achieve any of the disclosed therapies.

According to some techniques of this disclosure, both of a first device and a second device of a medical device system may determine an occurrence of a tachyarrhythmia, although this is not required. In some examples, the first device may determine the occurrence of a tachyarrhythmia based on sensed cardiac electrical signals, and may communicate the determination to the second device. In other examples, the second device may determine the occurrence of a tachyarrhythmia based on sensed cardiac electrical signals, and may communicate the determination to the first device. In yet other examples, the first device and the second device may both determine the occurrence of a tachyarrhythmia independently based on sensed cardiac electrical signals, and in still other examples, a device other than the first device and the second device may determine the occurrence of a tachyarrhythmia and may communicate the determination to the first device and/or the second device. Alternatively, one of the first and second devices may sense cardiac electrical signals, communicate those cardiac electrical signals to the other of the first and second devices, and the other of the first and second devices may use those received cardiac electrical signals to determine an occurrence of a tachyarrhythmia and may communicate that determination back to the first one of the first and second devices. The first and/or second devices may employ one or more techniques for determining occurrences of a tachyarrhythmia based on sensed cardiac electrical signals such as heart rate, a heart rhythm, ECG morphology, etc.

Additionally or alternatively, the first and/or second devices may determine occurrences of tachyarrhythmia based on one or more mechanical parameters of the patient, such as a heart contractility parameter, a heart sounds parameter, a cardiac output parameter, and/or a posture parameter. In some cases, the first and/or second devices may compare a heart contractility parameter to a contractility threshold. If the first and/or second devices determine that the heart contractility parameter is greater than (or, in some examples, less than) the contractility threshold, the first and/or second devices may determine an occurrence of a tachyarrhythmia. Additionally or alternatively, the first and/or second devices may compare a heart sounds parameter to a heart sounds threshold. If the first and/or second devices determine that the heart sounds parameter is greater than (or, in some examples, less than) the heart sounds threshold, the first and/or second devices may determine an occurrence of a tachyarrhythmia. Additionally or alternatively, the first and/or second devices may compare a cardiac output parameter to a cardiac output threshold. If the first and/or second devices determine that the cardiac output parameter is greater than (or, in some examples, less than) the cardiac output threshold, the first and/or second devices may determine an occurrence of a tachyarrhythmia. Additionally or alternatively, the first and/or second devices may compare a posture parameter to a posture threshold (e.g. a vertical posture parameter or a vertical posture threshold or a horizontal posture parameter to a horizontal posture parameter). If the first and/or second devices determine that the posture parameter is greater than (or, in some examples, less than) the posture threshold, the first and/or second devices may determine an occurrence of an arrhythmia.

Of course, the first and/or second devices may use a combination of the above described parameters in determining an occurrence of a tachyarrhythmia. For instance, the first and/or second devices may employ a hierarchical logic to determine an occurrence of a tachyarrhythmia. As one example, the first and/or second devices may use a first parameter to make an initial determination of an occurrence of a tachyarrhythmia, and may use a second parameter to confirm the initial determination before making a determination of an occurrence of a tachyarrhythmia. In other examples, the first and/or second devices may use additional parameters in making initial determinations or actual determinations. In other examples, the first and/or second devices may use a strict or weighted voting system using multiple of the parameters in making a determination of an occurrence of a tachyarrhythmia.

As one example, three of the parameters may indicate the occurrence of a tachyarrhythmia while two other parameters may not indicate an occurrence of a tachyarrhythmia. The first and/or second devices may then determine an occurrence of a tachyarrhythmia based on the greater number of parameters indicating an occurrence of a tachyarrhythmia. In other examples, the first and/or second devices may employ other, more complex, voting schemes to determine the occurrence of a tachyarrhythmia.

In some examples, the first and/or second devices may determine physiological parameters and/or occurrences of tachyarrhythmias based on information gathered by each device. For example, the first device may include one or more sensors that gather physiological parameters and/or an electrical sensing module that senses the cardiac electrical activity, and the first device may make one or more determinations based on the gathered information, such as determining whether a tachyarrhythmia is occurring. Alternatively, the first device may receive information, such as physiological parameters or sensed cardiac electrical activity from another device, for example the second device or another device of the system. In such examples, the first device may use the received information in determining physiological parameters and/or occurrences of, for example, tachyarrhythmias. In a similar manner, the second device may determine physiological parameters and/or occurrences of tachyarrhythmias based on information gathered by the second device or information received by the second device from other devices.

Figure 6:
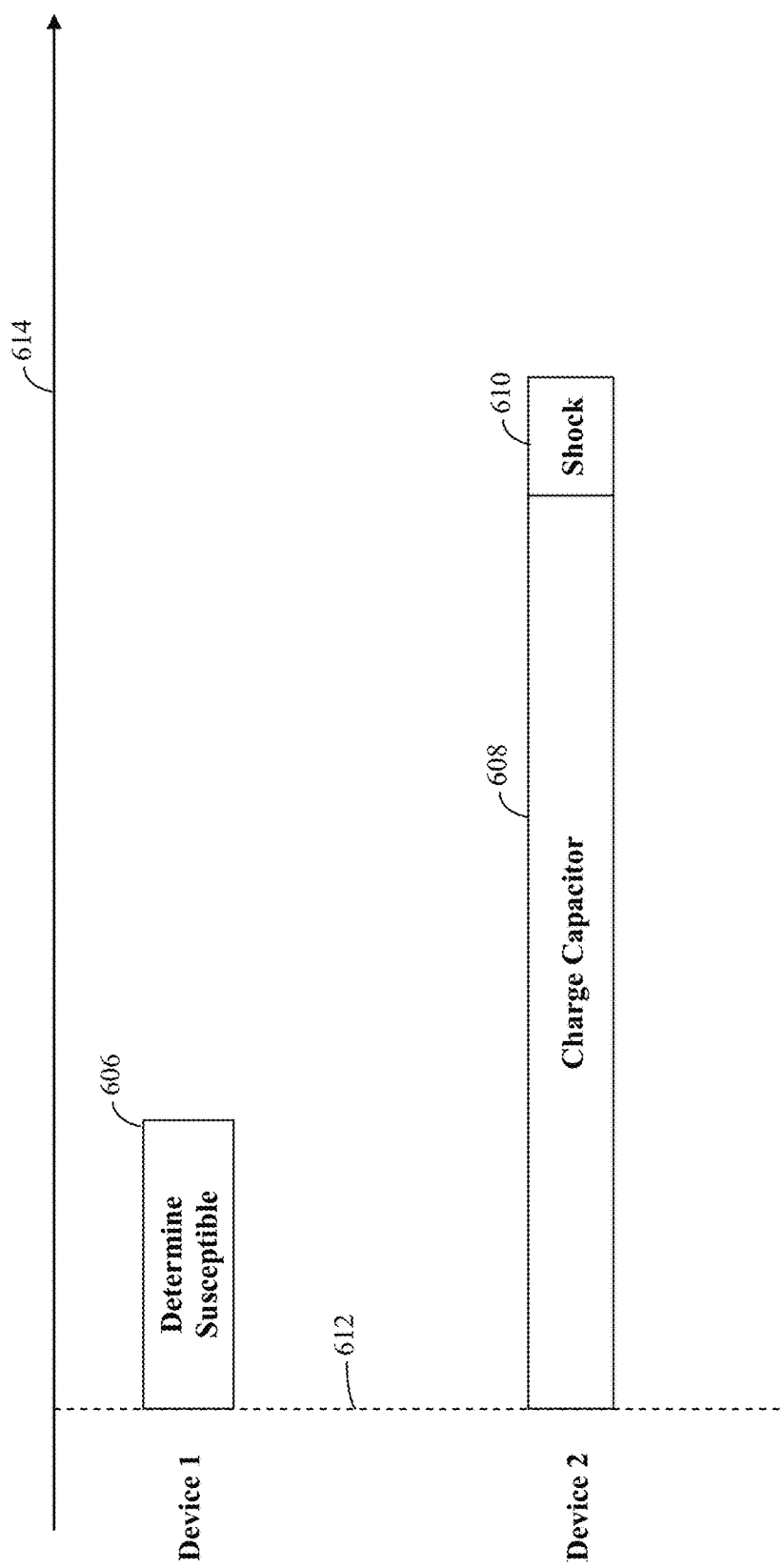
FIG. 6 is a timing diagram showing illustrative functions a first device and a second device may perform in relation to one another, in accordance with an example of the present disclosure.
Figure 7:
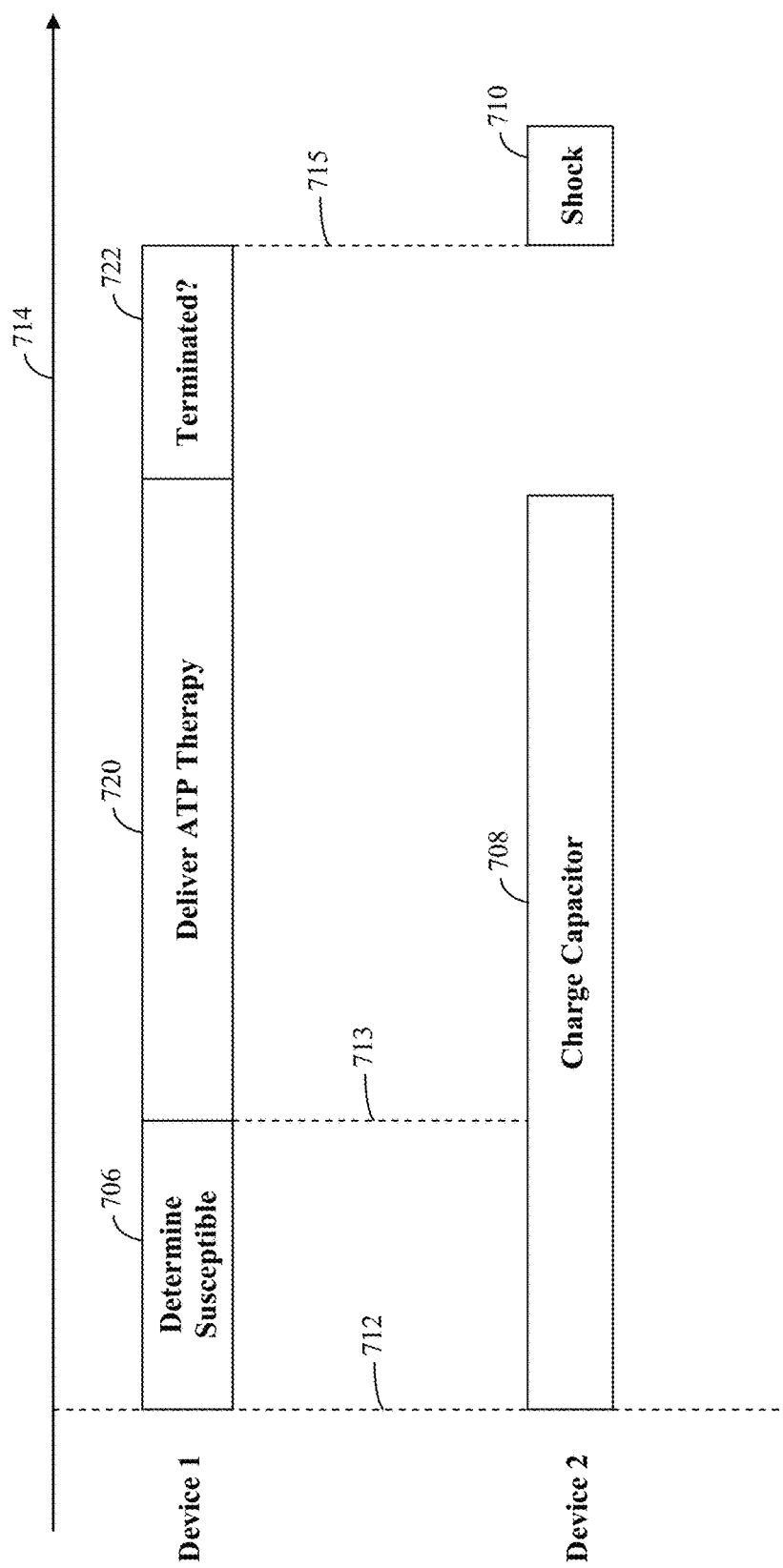
FIG. 7 is a timing diagram showing illustrative functions a first device and a second device may perform in relation to one another, in accordance with an example of the present disclosure.

FIGS. 6 and 7 illustrate one example operational technique for a first device and a second device for delivering electrical stimulation therapy to a heart of a patient. FIGS. 6 and 7 illustrate timelines 614 and 714, which include an onset of a tachyarrhythmia at times 612 and 712, along with various functions performed by Device 1 and Device 2. In the examples of FIGS. 6 and 7, Device 1 may be an LCP, such as LCP 100 described with respect to FIG. 1 and Device 2 may be MD 200 described with respect to FIG. 2. However, in other examples, Device 1 and Device 2 may represent other devices. Additionally, other systems may employ any disclosed techniques which include additional devices, for example diagnostic only devices.

In the examples of FIGS. 6 and 7, regardless of how a device 1 determines the occurrence of the tachyarrhythmia (e.g. either based on sensed cardiac electrical signals and/or based on a received determination of an arrhythmia from another device), device 1 may determine whether the tachyarrhythmia is susceptible to ATP therapy, as indicated by boxes 606 and 706. For example, device 1 may determine a heart rate parameter based on the sensed electrical signals. Device 1 may identify R-waves or QRS complexes, or other features to determine heart contractions. Device 1 may count these identified features for a period of time to determine how many of the features occur within the period of time, ultimately resulting in a heart rate in beats per minute. Device 1 may compare the heart rate to a heart rate threshold. If Device 1 determines that the heart rate is above a heart rate threshold, device 1 may determine that the detected tachyarrhythmia to not likely to be susceptible to ATP therapy. However, if device 1 determines that the heart rate is below the heart rate threshold, device 1 may determine that the detected tachyarrhythmia is likely to be susceptible to ATP therapy Additionally or alternatively, device 1 may determine a heart rhythm regularity parameter based on sensed cardiac electrical signals. The heart rhythm regularity parameter may be a measure of the regularity of the heart rate over time, and may be generated by monitoring the time between successive detected heart beats over a predetermined time period. If the heart rhythm regularity parameter is above a regularity threshold (e.g. sufficiently regular), device 1 may determine that the tachyarrhythmia is likely to be susceptible to ATP therapy. If the heart rhythm regularity parameter is below the regularity threshold (e.g. not sufficiently regular), device 1 may determine that the tachyarrhythmia is not likely to be susceptible to ATP therapy.

Additionally or alternatively, device 1 may determine a morphology parameter for sensed cardiac signal. The morphology parameter may indicate a difference in signal morphology of detected QRS complexes relative to one or more morphology templates. If device 1 determines that the difference in signal morphology of detected QRS complexes relative to the one or more morphology templates is greater than a morphology threshold, device 1 may determine that the tachyarrhythmia is likely to be susceptible to ATP therapy. If device 1 determines that the difference in signal morphology of detected QRS complexes relative to the one or more morphology templates is less than a morphology threshold, device 1 may determine that the tachyarrhythmia is not likely to be susceptible to ATP therapy. In at least some of these examples, device 1 may determine whether the morphology of the sensed cardiac signal is monomorphic. If device 1 determines that the morphology of the sensed cardiac signal is monomorphic, device 1 may determine that the tachyarrhythmia is susceptible to ATP therapy.

In some instances, device 1 may have access to both atrial cardiac electrical signals and ventricular cardiac electrical signals. For instance, device 1 may have multi-sensing capabilities, where device 1 is able to identify signals representative of ventricular contraction and signals representative of atrial contraction. In other examples, device 1 may receive information relating to contraction of other heart chambers (e.g. heart chambers other than the heart chamber within which device 1 is implanted) from one or more other devices, such as other LCPs, an S-ICD or other medical devices. When so provided, device 1 may determine whether the ventricular beat rate is greater than the atrial beat rate. If device 1 determines that the ventricular beat rate is greater than the atrial beat rate, perhaps by a threshold amount, device 1 may determine that the tachyarrhythmia is likely to be susceptible to ATP therapy. If device 1 determines that the ventricular beat rate is not greater than the atrial beat rate, perhaps by a threshold amount, device 1 may determine that the tachyarrhythmia is not likely to be susceptible to ATP therapy. Of course, device 1 may use a combination of the above described parameters (e.g. heart rate, rhythm regularity, morphology, ventricular versus atrial beat rate) in determining whether the tachyarrhythmia is likely to be susceptible to ATP therapy, possibly using a strict or weighted voting system. In at least some examples, device 1 may determine that a tachyarrhythmia is likely to be susceptible to ATP therapy if the heart rate parameter is less than two-hundred forty beats per minute (240 bpm), the rhythm is sufficiently regular (<10 bpm deviation), and the morphology parameter is less than the morphology threshold (which may indicate morphologically similar QRS complexes).

In some cases, a device 2 may determine the occurrence of the tachyarrhythmia. Regardless of how a device 2 determines the occurrence of the tachyarrhythmia (e.g. either based on sensed cardiac electrical signals and/or based on a received determination of an arrhythmia from another device), device 2 may begin a defibrillation shock therapy program. For example, device 2, upon determining an occurrence of a tachyarrhythmia, device 2 may begin charging a capacitor to a predefined energy level, as indicated by boxes 608 and 708. Once the capacitor has charged to the predefined energy level, device 2 may deliver one or more defibrillation pulses to the heart of the patient in an attempt to terminate the tachyarrhythmia, as indicated by boxes 610 and 710. The capacitor may be part of a pulse generator module of device 2.

The predefined energy level for the capacitor may represent a specific number of joules of energy. In some cases, device 2 may be programmed with a single specific predefined energy level. In other cases, device 2 may include logic dictating a selection of one of a number of predefined energy levels based on one or more parameters such as a heart rate, the morphology of the tachyarrhythmia, battery level and/or any other suitable parameter. In some cases, device 2 may be configured to deliver defibrillation shocks of increasing energy until the arrhythmia terminates, which may also affect the specific predefined energy level for the capacitor.

The defibrillation shock therapy program may be modified on the fly. For instance, device 1 may communicate information to device 2 which may affect the defibrillation shock therapy program. For example, some tachyarrhythmias may be treatable by delivering ATP therapy to the heart of the patient, which is sometimes preferable to delivering defibrillation shock therapy. In the example shown in FIGS. 6 and 7, device 2 may be configured to receive a "suspend" signal or command from device 1, wherein after receiving the "suspend" command, device 2 suspends the shock portion of the defibrillation shock therapy program. In some cases, device 2 may continue to charge the capacitor up to the predefined energy level, but the delivery of one or more defibrillation pulses may be suspended until receiving another command from device 1 (or another device), such as a resume command.

In examples where at least device 2 communicates messages and/or data to device 1, device 2 may transmit any messages and/or data via one or more transmit communication vectors. For example, device 1 and device 2 may include a system such as depicted in FIG. 3, where device 1 is an LCP, e.g. LCP 302, and device 2 is represented by pulse generator 306, which may be an S-ICD as described with respect to FIG. 2. In such a system, device 2 may have a number of electrodes disposed on a subcutaneously implanted lead, such as electrodes 308a-308c, and one or more other electrodes secured to the housing (as described with respect to FIGS. 1 and 2). According to some examples, when device 2 transmits messages and/or data to device 1, device 2 may deliver the information via a transmit communication vector that includes shock electrode 308c and an electrode disposed on the housing (e.g. can) of pulse generator 306. However, in other examples, device 2 may deliver the information via a transmit communication vector that includes sense electrode 308a and an electrode disposed on the housing (e.g. can) of pulse generator 306, or sense electrode 308b and an electrode disposed on the housing (e.g. can) of pulse generator 306. In still other examples, device 2 may deliver the information via a transmit communication vector that includes sense electrodes 308a and 308b, or either sense electrode 308a-b and shock electrode 308c. Additionally, in some examples, device 2 may include more than one electrode disposed on its housing (e.g. can). In such examples, additional transmit communication vectors may be made from pairing any of the electrodes 308a-c to any of the electrodes disposed on the housing of device 2. In some cases, device 1 and/or device 2 may automatically select an appropriate transmit communication vector. For example, device 1 and/or device 2 may be programmed to minimize communication power, maximize signal-to-noise ratio, minimize undesirable tissue stimulation (e.g. heart capture, phrenic stimulation), optimize impedance, and/or achieve some balance of these and/or other characteristics. In some cases, device 1 and/or device 2 may collect and send information to a physician so that the physician can manually select an appropriate transmit communication vector.

Additionally, in examples where device 1 also transmits messages or data to device 2, device 2 may sense for messages and/or data from device 1 via one or more sense communication vectors. In some examples, the sense communication vector may be the same as the transmit communication vector. However, in other examples, device 2 may sense for messages and/or data from device 1 via a sense communication vector that differs from the transmit communication vector via which device 2 transmits messages and/or data to device 1. For example, if device 2 transmits messages and/or data via a transmit communication vector that includes a shock electrode 308c and an electrode disposed on the housing (e.g. can) of pulse generator 306, device 2 may sense for messages and/or data from device 1 via a sense communication vector that includes sense electrodes 308a and 308b. However, device 2 may use other sense communication vectors for sensing messages and/or data as desired, including all other combinations of electrodes other than shock electrode 308c and the corresponding electrode disposed on the housing (e.g. can) of device 2. Accordingly in such examples, device 2 may sense for messages and/or data from device 1 via any sense communication vector that includes a pair of electrodes which differs from the pair of electrodes that include the transmit communication vector.

FIG. 6 illustrates an example where Device 1 determines that a detected tachyarrhythmia is not likely to be susceptible to ATP therapy. Accordingly, device 1 does not communicate a "suspend" command to device 2, and device 2 continues to charge the capacitor. Upon charging the capacitor to the predefined energy level, device 2 delivers one or more defibrillation pulses, as shown at 610.

FIG. 7 illustrates an example where device 1 determines that a detected tachyarrhythmia is likely to be susceptible to ATP therapy. Accordingly, device 1 sends a "suspend" command, as represented by line 713, to device 2. This suspend command may be sent using a telemetry module of device 1. The suspend command may be received via a telemetry module of device 2. In response, device 2 may continue to charge the capacitor to the predefined energy level, but may not immediately deliver the one or more defibrillation pulses after the capacitor reaches the predefined energy level. Instead, device 2 may enter a wait state. Device 1 may then deliver ATP therapy to the heart of the patient, as indicated by box 720. In some instances, device 1 may be configured to only deliver ATP therapy for a period of time less than the time it takes to charge the capacitor to the predefined energy level. In other instances, device 1 may be configured to deliver ATP therapy for a longer or shorter time period, as desired. After delivering the ATP therapy, device 1 and/or device 2 may determine whether the delivered ATP therapy terminated the tachyarrhythmia. If the ATP therapy did not terminate the tachyarrhythmia, device 1 may communicate a "resume" or "shock" command to device 2, as indicated by line 715. Once device 2 receives the resume or shock command, device 2 may deliver one or more defibrillation pulses to the heart of the patient in accordance with the defibrillation shock therapy program, as indicated by box 710.

In instances where the ATP therapy did terminate the tachyarrhythmia at block 722, device 1 may communicate an "abort" command to device 2 instead of a resume or shock command. After receiving an "abort" command, device 2 may cease the defibrillation shock therapy program, and not deliver defibrillation pulses to the heart of the patient. The capacitor may be discharged in a safe manner.

In some cases, instead of relying on device 1 for a resume or shock command in order for device 2 to deliver one or more defibrillation pulses following a suspend command, device 2 may determine on its own whether the delivered ATP therapy terminated the tachyarrhythmia. For example, after receiving a "suspend" command, device 2 may monitor the delivery of ATP therapy by device 1. After device 1 finishes delivering ATP therapy, device 2 may determine on its own whether the ATP therapy was successful. If device 2 determines that the ATP therapy was not successful, device 2 may continue on with any defibrillation shock therapy program and deliver one or more defibrillation pulses. If device 2, however, determines that the ATP therapy was successful, device 2 may abort the defibrillation shock therapy program and safely discharge the capacitor.

In some cases, rather than monitoring the delivery of ATP therapy by device 1, device 2 may be configured to wait a predetermined period of time after receiving a "suspend" command to determine whether the tachyarrhythmia is still occurring. If the tachyarrhythmia is still occurring after the expiration of the predetermined period of time, device 2 may continue with the defibrillation shock therapy program and deliver one or more defibrillation pulses to the heart of the patient. If the tachyarrhythmia is not still occurring, device 2 may abort the defibrillation shock therapy program and safely discharge the capacitor. In still other examples, device 2 may employ such a timing mechanism in addition to the command communications between device 1 and device 2 as a backup mechanism.

In yet another alternate example, there may be no communication between device 1 and device 2. For example, device 1 may not send any "suspend" or "resume" or "shock" commands to device 2, and neither device may communicate determinations of tachyarrhythmias to each other. For example, both device 1 and device 2 may independently determine an occurrence of a tachyarrhythmia. Device 1 may then determine whether the tachyarrhythmia is susceptible to ATP therapy and, if so, deliver ATP therapy. Device 2 may begin charging a capacitor and, either just before the capacitor is finished charging or after the capacitor has finished charging, device 2 may determine whether the tachyarrhythmia is still occurring. If the arrhythmia is still occurring, device 2 may then deliver one or more defibrillation pulses to the heart. In some examples, device 2 may be configured to wait a predetermined amount of time after the capacitor is finished charging before determining whether the tachyarrhythmia is still occurring. In such examples, the time taken for the capacitor to charge may give device 1 enough time to determine whether to deliver ATP therapy and to attempt to terminate the tachyarrhythmia before device 2 delivers one or more defibrillation pulses. Additionally, withholding the defibrillation until after ATP therapy has been attempted, in at least some instances, may be safer for a patient. In this manner, device 1 and device 2 may operate in concert with each other to deliver coordinated electrical stimulation therapy without actually requiring the sending of communication signals between the devices.

Figure 8:
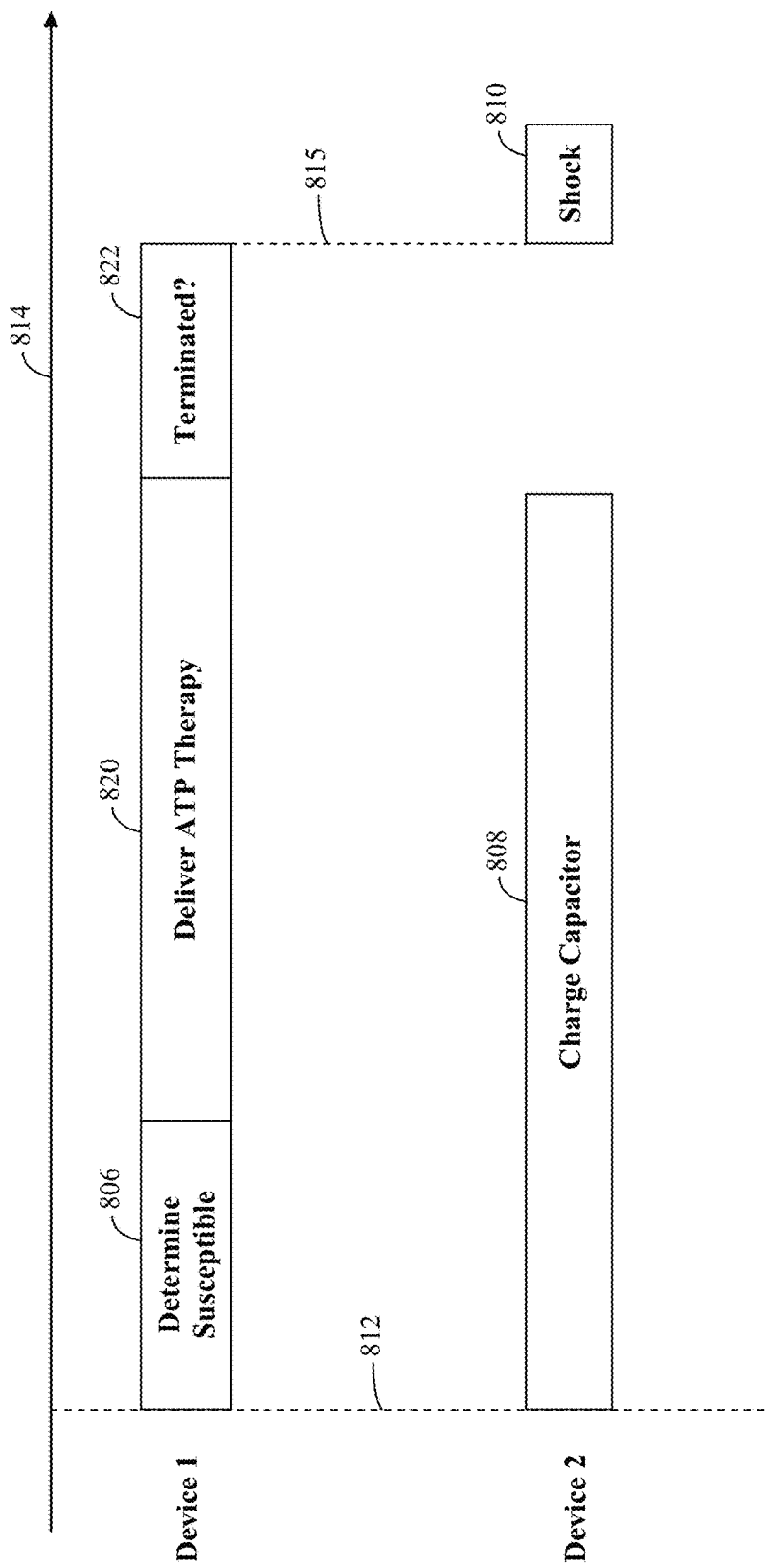
FIG. 8 is a timing diagram showing illustrative functions a first device and a second device may perform in relation to one another, in accordance with an example of the present disclosure.
Figure 9:
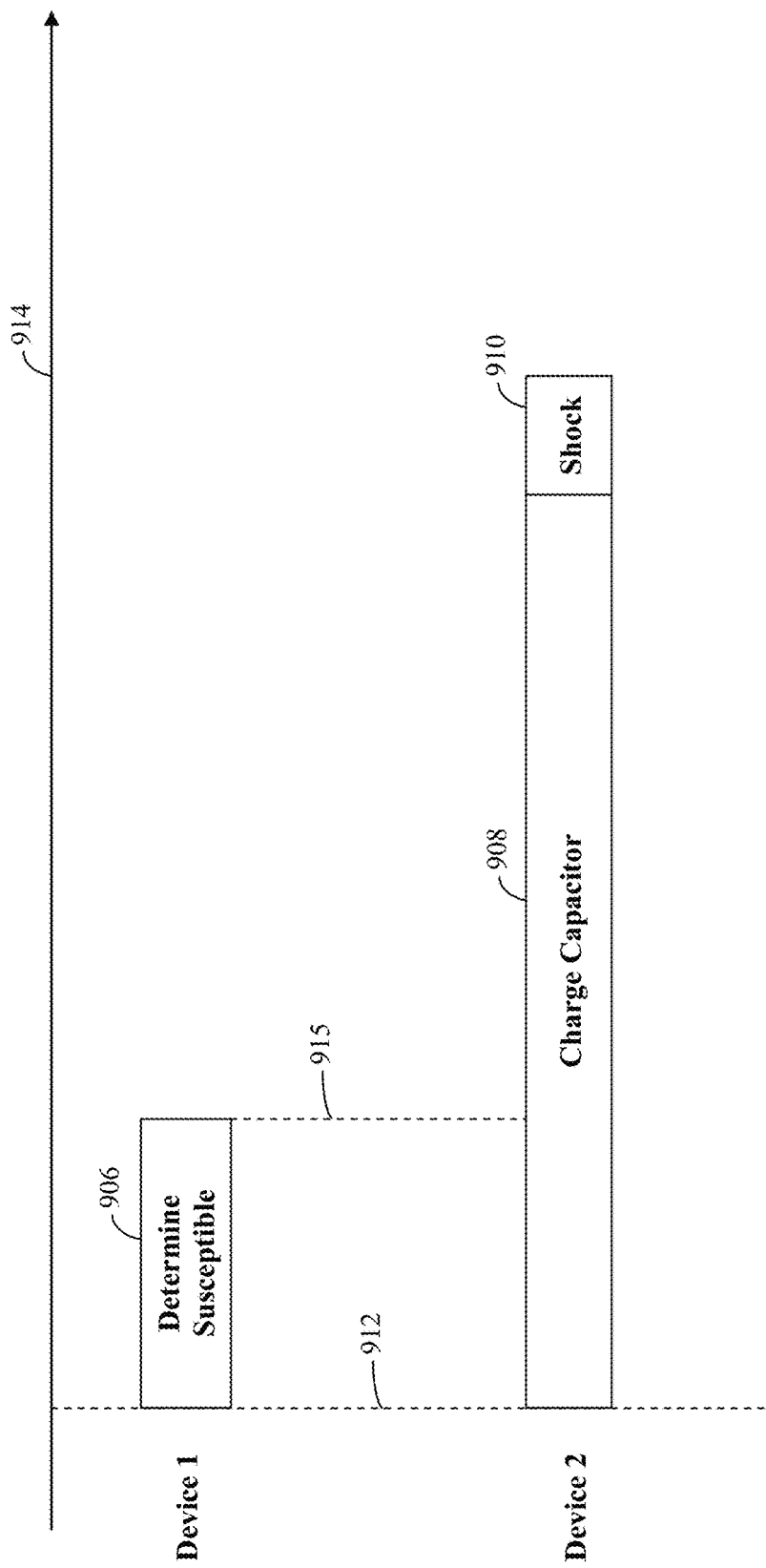
FIG. 9 is a timing diagram showing illustrative functions a first device and a second device may perform in relation to one another, in accordance with an example of the present disclosure.

FIGS. 8 and 9 illustrate another example operational technique for delivering electrical stimulation therapy to a heart of a patient. FIGS. 8 and 9 illustrate timelines 814 and 914, which include an onset of a tachyarrhythmia at times 812 and 912, along with various functions performed by Device 1 and Device 2. In the examples of FIGS. 8 and 9, device 1 may be an LCP, such as LCP 100 described with respect to FIG. 1 and device 2 may be MD 200 described with respect to FIG. 2. However, in other examples, device 1 and device 2 may represent other devices. Additionally, other systems may employ any disclosed techniques which include additional devices, for example diagnostic only devices.

As with the examples of FIGS. 6 and 7, in the examples of FIGS. 8 and 9, after determining the occurrence of the tachyarrhythmia at times 812 and 912, device 1 may begin to determine whether the tachyarrhythmia is likely to be susceptible to ATP therapy, as indicated by boxes 806 and 906. Additionally, after determining the occurrence of the tachyarrhythmia at times 812 and 912, device 2 may begin a defibrillation shock therapy program. For example, device 2 may begin to charge a capacitor to a predefined energy level, as indicated by boxes 808 and 908. Unlike the examples of FIGS. 6 and 7, in the examples of FIGS. 8 and 9, device 2 may not deliver one or more defibrillation pulses to the heart of the patient until receiving a command from device 1.

FIG. 8 illustrates an example where device 1 determines that the detected tachyarrhythmia is likely to be susceptible to ATP therapy. Accordingly, device 1 may deliver ATP therapy, as indicated by box 820. In some instances, device 1 may be configured to only deliver ATP therapy for a period of time less than the time it takes to charge the capacitor to the predefined energy level. However, in other instances, device 1 may be configured to deliver ATP therapy regardless of time it takes to charge the capacitor. After delivering ATP therapy, device 1 may determine whether the ATP therapy terminated the tachyarrhythmia, as indicated by box 822. If device 1 determines that the ATP therapy failed to terminate the tachyarrhythmia, device 1 may communicate a "shock" command to device 2, as indicated by line 815. Device 2, after charging the capacitor to the predefined energy level, may deliver one or more defibrillation pulses in accordance with the defibrillation shock therapy program, as indicated by box 810. In cases where device 1 determines that the ATP therapy was successful in terminating the tachyarrhythmia, device 1 may send an "abort" command to device 2 instead of a resume or shock command. Upon receiving an "abort" command, device 2 may cease the defibrillation shock therapy program, and not deliver defibrillation pulses to the heart of the patient.

As with the examples of FIGS. 6 and 7, instead of relying on device 1 for a resume or "shock", device 2 may determine on its own whether the delivered ATP therapy terminated the tachyarrhythmia. For example, device 2 may be configured to wait a predetermined period after determining an occurrence of a tachyarrhythmia and then determine whether the tachyarrhythmia is still occurring. If the tachyarrhythmia is still occurring after the expiration of the predetermined period of time, device 2 may continue with the defibrillation shock therapy program and deliver one or more defibrillation pulses to the heart of the patient. If the tachyarrhythmia is not still occurring, device 2 may abort the defibrillation shock therapy program and safely discharge the capacitor. Although, in other examples, device 2 may employ such a timing mechanism in addition to the command communications between device 1 and device 2 as a backup mechanism.

FIG. 9 illustrates an example where device 1 determines that the tachyarrhythmia is not susceptible to ATP therapy. Accordingly, device 1 may communicate a "shock" command to device 2, as indicated by line 915. Where device 2 has not yet finished charging the capacitor, as illustrated in FIG. 9, device 2 may finish charging the capacitor before delivering one or more defibrillation pulses in accordance with the defibrillation shock therapy program as indicated by box 910. However, if device 2 has already finished charging the capacitor before receiving the "shock" command, device 2 may immediately deliver one or more defibrillation pulses in accordance with the defibrillation shock therapy program.

Figure 10:
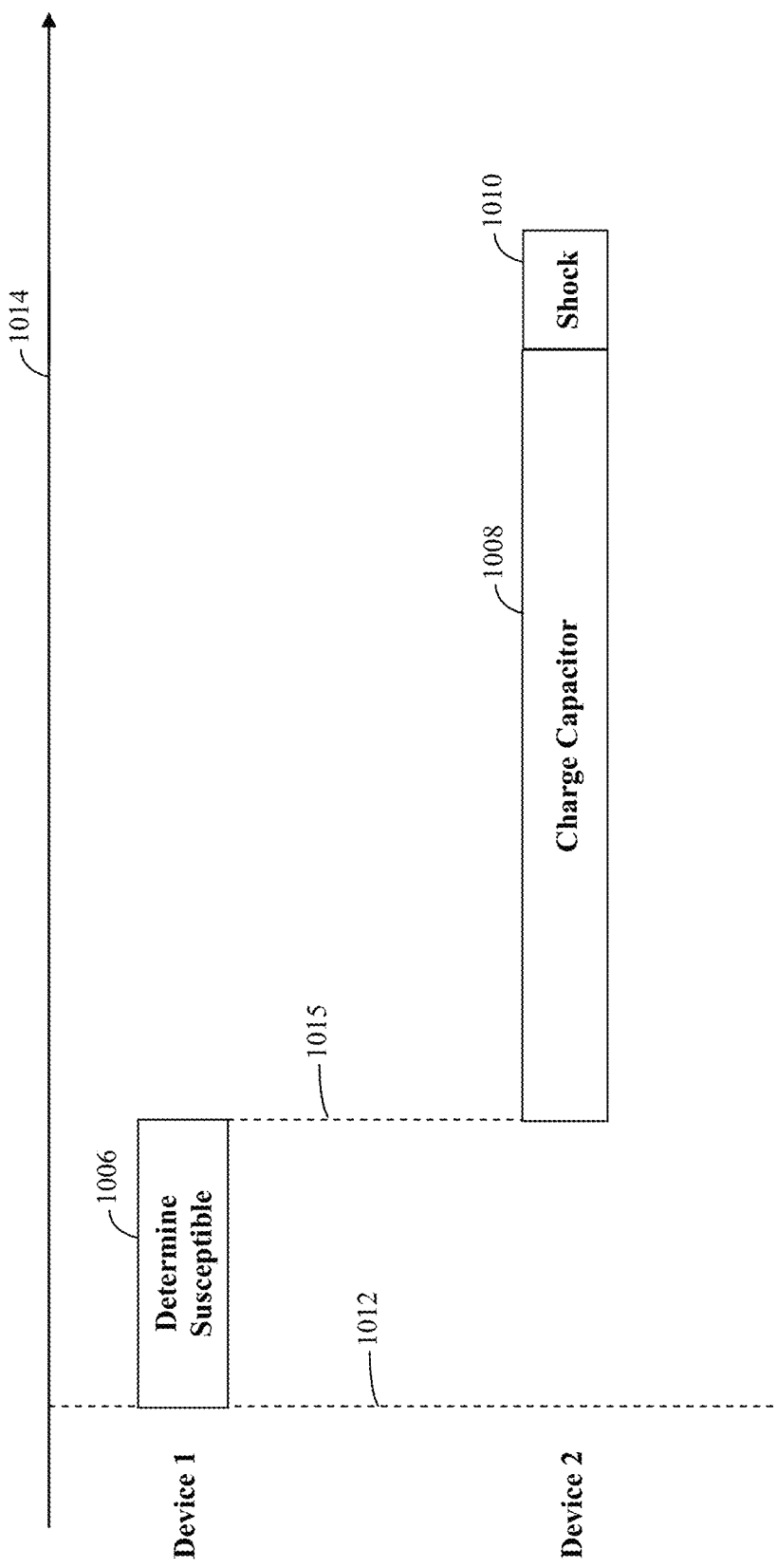
FIG. 10 is a timing diagram showing illustrative functions a first device and a second device may perform in relation to one another, in accordance with an example of the present disclosure.
Figure 11:
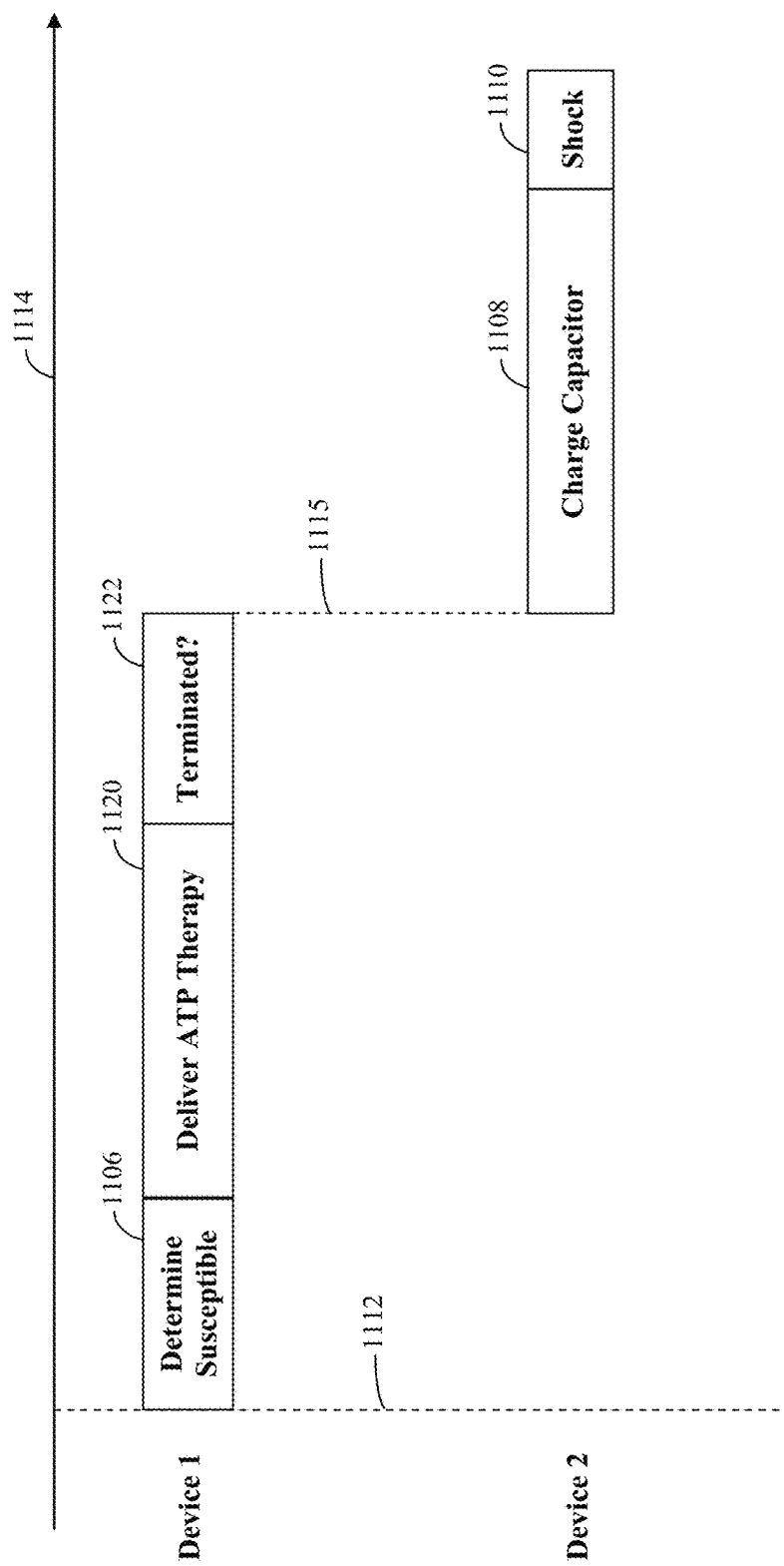
FIG. 11 is a timing diagram showing illustrative functions a first device and a second device may perform in relation to one another, in accordance with an example of the present disclosure.

FIGS. 10 and 11 illustrate another example operational technique for delivering electrical stimulation therapy to a heart of a patient. FIGS. 10 and 11 illustrate timelines 1014 and 1114, which include an onset of a tachyarrhythmia at times 1012 and 1112, along with various functions performed by device 1 and device 2. In the examples of FIGS. 10 and 11, device 1 may be an LCP, such as LCP 100 described with respect to FIG. 1, and device 2 may be MD 200 such as described with respect to FIG. 2. In other examples, device 1 and/or device 2 may represent other devices, such as diagnostic only device.

As with the examples of FIGS. 6 and 7, in the examples of FIGS. 10 and 11, after determining the occurrence of a tachyarrhythmia at times 1012 and 1112, device 1 may begin to determine whether the tachyarrhythmia is likely to be susceptible to ATP therapy, as indicated by boxes 1006 and 1106. Unlike the examples of FIGS. 6 and 7, device 2 may not take any action until receiving a command from device 1.

FIG. 10 depicts an example where device 1 determines that a tachyarrhythmia is not likely to be susceptible to ATP therapy. Accordingly, device 1 may send a "shock" command to device 2, as represented by line 1015. In the example of FIG. 10, only after device 2 has received the "shock" command from device 1, does device 2 begin the defibrillation shock therapy program, starting with charging the capacitor to a predefined energy level, as shown by box 1008. Once the capacitor has been charged to the predefined energy level, device 2 may deliver one or more defibrillation pulses to the heart of the patient in accordance with the defibrillation shock therapy program, as shown by box 1010.

FIG. 11 depicts an example where device 1 determines that the tachyarrhythmia is likely to be susceptible to ATP therapy. Here, device 1 may deliver ATP therapy to the heart of the patient, as indicated by box 1120. Device 1 may then determine whether the ATP therapy was successful in terminating the tachyarrhythmia, as indicated by box 1122. In the example of FIG. 11, device 1 has determined that the ATP therapy was not successful in terminating the tachyarrhythmia. Accordingly, device 1 may send a "shock" command to device 2 as indicated by line 1115. Device 2 may then begin charging a capacitor to a predefined energy level, as indicated by box 1108. Device 2 may then, after having charged the capacitor to the predefined energy level, deliver one or more defibrillation shocks to the heart of the patient in accordance with the defibrillation shock therapy program, as shown by box 1110. In the event that device 1 determines that the ATP therapy was successful in terminating the tachyarrhythmia, device 1 may not send a "shock" command to device 2.

Figure 12:
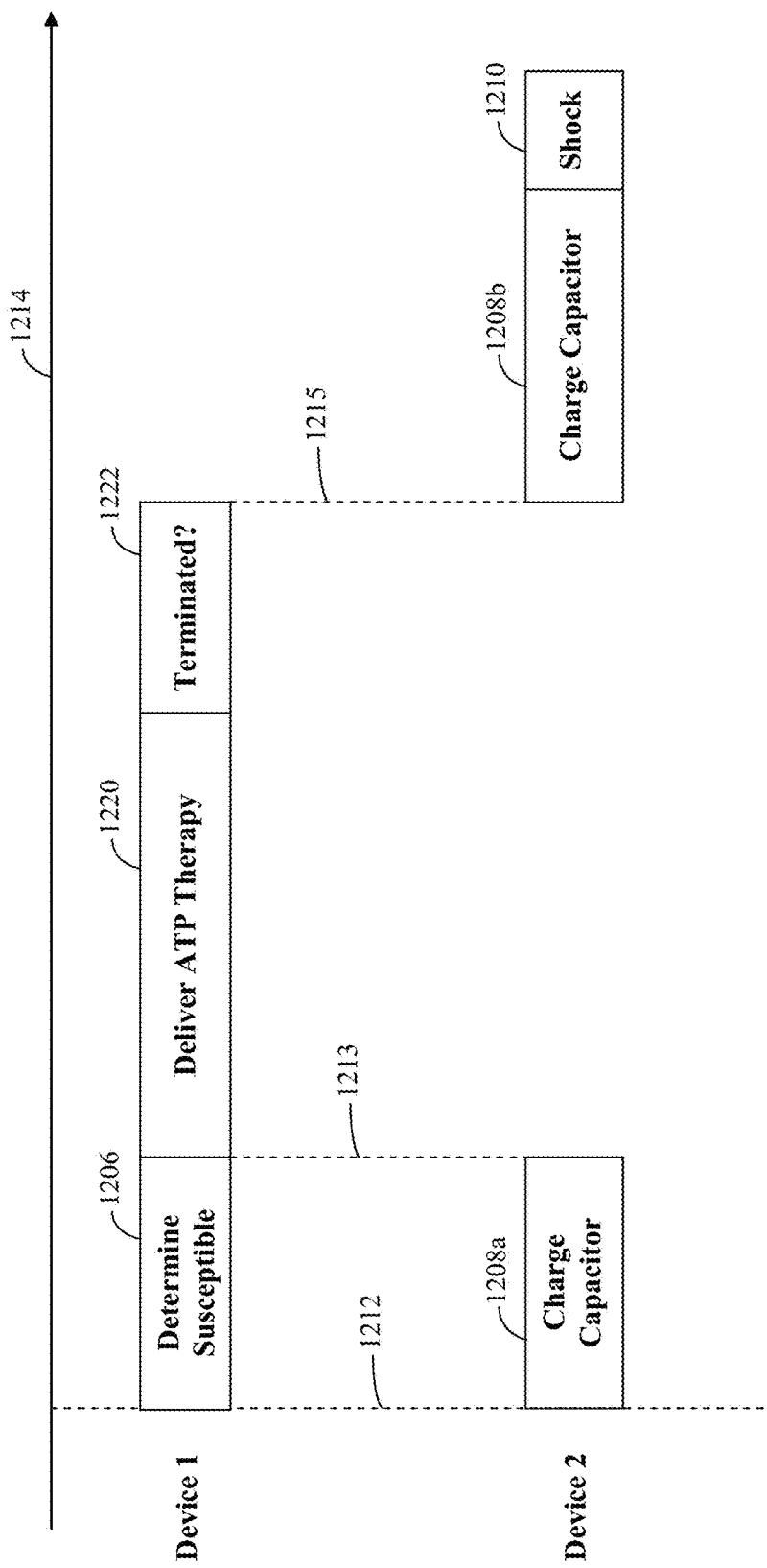
FIG. 12 is a timing diagram showing illustrative functions a first device and a second device may perform in relation to one another, in accordance with an example of the present disclosure.

FIG. 12 illustrates another example operational technique for delivering electrical stimulation therapy to a heart of a patient. FIG. 12 illustrates timeline 1214, which includes an onset of a tachyarrhythmia at time 1212, along with various functions performed by device 1 and device 2. In the example of FIG. 12, device 1 may be an LCP, such as LCP 100 described with respect to FIG. 1, and device 2 may be MD 200 such as that described with respect to FIG. 2.

As with the examples of FIGS. 6 and 7, in the example of FIG. 12, after determining the occurrence of the tachyarrhythmia at time 1212, device 1 may begin to determine whether the detected tachyarrhythmia is likely to be susceptible to ATP therapy, as indicated by box 1206. In this case, device 2 may also detect the occurrence of the tachyarrhythmia at time 1212, either on its own or with the aid of device 1 and/or another device. After determining the occurrence of a tachyarrhythmia at time 1212, device 2 may begin a defibrillation shock therapy program. For example, device 2 may begin to charge a capacitor to a predefined energy level, as indicated by boxes 1208*a* and 1208*b*.

Unlike the examples of FIGS. 6 and 7, in the example of FIG. 12, device 1 may issue a "suspend" command if device 1 determine that the detected tachyarrhythmia is likely to be susceptible to ATP therapy. In some cases, the "suspend" command may cause device 2 to suspend charging the capacitor as shown, while in other case the "suspend" command may not suspend the charging of the capacitor.

Referring specifically to the example shown in FIG. 12, if device 1 determines that the tachyarrhythmia is likely to be susceptible to ATP therapy, device 1 may communicate a "suspend" command to device 2, as indicated by line 1213. This "suspend" command may cause device 2 to suspend charging the capacitor, as indicated by box 1208*a*. Device 1 may then deliver ATP therapy to the heart of the patient, as indicated by box 1220. If device 1 determines that the ATP therapy was successful in terminating the tachyarrhythmia, device 1 may send an "abort" command to device 2, instead of a "shock" command. Upon receiving the "abort" command, device 2 may cease the defibrillation shock therapy program, e.g. not deliver defibrillation pulses, and discharge the capacitor in a safe manner. However, if device 1 determines that the ATP therapy failed to terminate the tachyarrhythmia as indicated by box 1222, device 1 may communicate a "shock" command to device 2, as indicated by line 1215.

Upon receiving a "shock" command, device 2 may continue to charge the capacitor to the predefined energy level, as indicated by box 1208*b*. Once device 2 has charged the capacitor to the predefined energy level, device 2 may then deliver one or more defibrillation shocks to the heart of the patient in accordance with the defibrillation shock therapy program, as indicated by box 1210.

As with previous examples, instead of relying on device 1 for a "shock" command in order for device 2 to finish charging the capacitor to the predefined energy level, device 2 may be configured to wait a predetermined period of time after receiving the "suspend" command to determine whether the tachyarrhythmia is still occurring. If the tachyarrhythmia is still occurring after the expiration of the predetermined period of time, device 2 may then continue to charge the capacitor to the predefined energy level and then deliver one or more defibrillation pulses to the heart of the patient. If the tachyarrhythmia is not still occurring, device 2 may abort the defibrillation shock therapy program and safely discharge the capacitor. In some instances, device 2 may employ such a timing mechanism in addition to the command communications between device 1 and device 2 as a backup mechanism.

As mentioned previously, the examples of FIGS. 6-12 should not be viewed as limiting the techniques disclosed herein to a system with only two medical devices, or even to the specific splitting of functions depicted in FIGS. 6-12. For instance, as described previously, a system employing the disclosed techniques may include a third device which communicates determinations of arrhythmias to device 1 and/or device 2. In another example, device 2 may include capabilities for performing ATP therapy. In such examples, device 1 may be a diagnostic only device. Device 1 may still make determinations about susceptibility or whether delivered ATP therapy was successful, but device 2 may actually perform the ATP therapy (device 1 may also still communicate the various commands to device 2). These are just some examples of differences from the specific depicted examples that should be understood to be within the spirit of this disclosure.

Another variation on the above described techniques is that instead of taking action based on determinations of tachyarrhythmias, device 1 and/or device 2 may take action based on electrical activity which may precede occurrences of tachyarrhythmias. As one example, device 1 and/or device 2 may analyze cardiac electrical activity to detect T-wave alternans. T-wave alternans have periodic beat-to-beat variation in the amplitude or morphology of the T-wave. Upon determining an occurrence of T-wave alternans (either through direct analysis of the cardiac electrical activity or based on a received determination of an occurrence of T-wave alternans), device 1 and/or device 2 may adjust the electrical stimulation therapy protocol used after determining an occurrence of a tachyarrhythmia. For example, since T-wave alternans are more closely associated with polymorphic ventricular tachycardia than monomorphic ventricular tachycardia, a system comprised of device 1 and device 2 may be configured to eliminate the step of determining whether the determined tachyarrhythmia is susceptible to ATP therapy. Instead, the system may proceed directly to shock therapy after determining an occurrence of an arrhythmia. In some examples, the system may compare the detected T-wave alternans to a predetermined threshold, for example a difference in amplitude or morphology of the T-waves of consecutive beats, and may only eliminate determining whether a tachyarrhythmia is susceptible to ATP therapy and proceeding directly to shock therapy if the difference in amplitude and/or morphology of the T-waves is greater than the predetermined threshold.

In other examples, device 1 and device 2 may take action based on changes to determined physiological parameters instead of determinations of occurrences of tachyarrhythmias. For instance, rather than using any determined physiological parameters to determine occurrences of tachyarrhythmias, as described previously, device 1 and/or device 2 may monitor one or more physiological parameters and take one or more actions directly based on any change in one or more physiological parameters. Such physiological parameters may include, but are not limited to, contractility, heart sounds, cardiac output, and posture.

One example of how such physiological information may be used relates to if cardiac output drops below a predetermined level. In such examples, the system could be configured to eliminate any steps of determining whether an arrhythmia would be susceptible to ATP therapy or any other attempt at classification. Additionally or alternatively, the system may eliminate any steps of attempting ATP therapy and proceed directly to delivering shock therapy when appropriate. Such a modification to the shock therapy protocol may reduce the likelihood of the patient losing consciousness. In another example, the system may determine during pulseless electrical activity (PEA) (a.k.a. electromechanical dissociation) which occurs when a heart rhythm is observed on an electrocardiogram that should be producing a mechanical contraction of the heart, but is not. PEA can be detected by device 1 and/or device 2 by the detection of R-waves but lack of detection of any mechanical cardiac motion (e.g. heart sounds, blood pressure changes, heart wall motion). Since neither shock therapy nor ATP therapy are effective treatments for PEA, the system may switch to a mode where the system is configured to not deliver any electrical stimulation therapy, regardless of any indications of arrhythmias based on sensed electrical activity or other physiological parameters. The system could be also be configured to immediately contact emergency medical personal.

In yet other examples, instead of, or in addition to, communicating the previously described "suspend", "shock", and/or "abort" commands, device 1 may be configured to modify the defibrillation shock therapy program of device 2 in other ways. For example, device 1 may communicate a specific predefined energy level to device 2, and device 2 may charge the capacitor to the received predefined energy level instead of the predefined energy level device 2 had determined. In some cases, this may operate to shorten the time for the device to deliver the one or more defibrillation pulses in accordance with the defibrillation shock therapy program. Device 1 may additionally or alternatively communicate commands to device 2 which alter other aspects of the defibrillation shock therapy program, such as the number of defibrillation pulses, the amplitude of the defibrillation pulses, the pulse width of the defibrillation pulses, the phases of the defibrillation pulses, and/or other morphological features of the defibrillation pulses. Device 1 may alter such aspects of the defibrillation shock therapy program based on the heart rate parameter, the morphology parameter, the rhythm regularity parameter, any of the physiological parameters discussed above, or any combination of such parameters.

Figure 13:
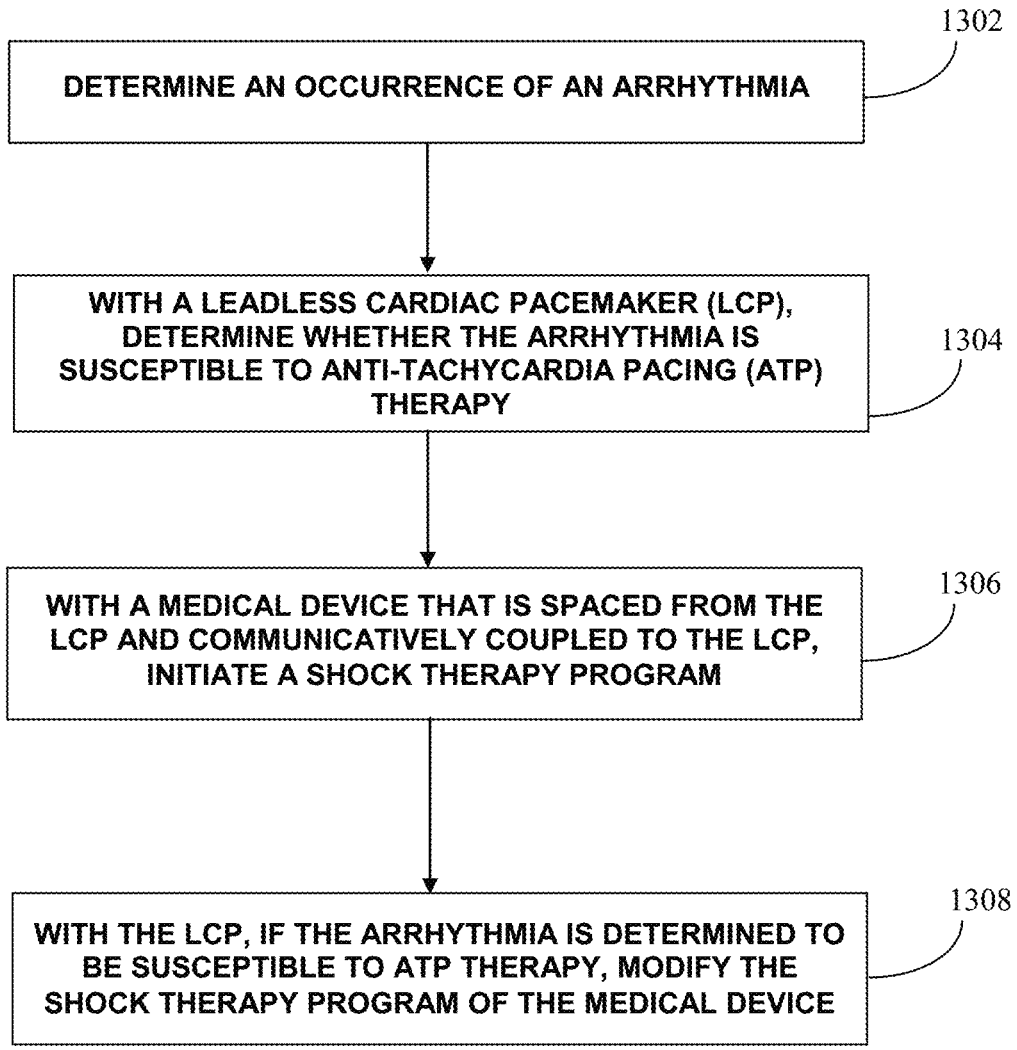
FIG. 13 is a flow diagram of an illustrative method that may be implemented by a medical device or medical device system, such as the illustrative medical devices and medical device systems described with respect to FIGS. 1-4.

FIG. 13 is a flow diagram of an illustrative method that may be implemented by an implantable medical device, such as shown in FIGS. 1 and 2, or a medical device system such as shown in FIGS. 3 and 4. Although the method of FIG. 13 will be described with respect to LCP 100, the illustrative method of FIG. 13 may be performed using any suitable medical device or medical device system.

In some instances, a first implantable medical device, for instance LCP 100, may be implanted in a first chamber of a heart, such as an atrium or ventricle, and may receive signals related to one or more physiological conditions of a patient. The received signals may be signals received at the one or more electrodes of the LCP 100. The received signals may be physiological signals directly sensed by the one or more electrodes of the LCP 100, and/or signals communicated to the LCP from another medical device, such as MD 200.

The LCP 100 may also be configured to determine an occurrence of an arrhythmia, as shown at 1302. LCP 100 may further determine whether the arrhythmia is susceptible to anti-tachycardia pacing (ATP) therapy, as shown at 1304. Another medical device that is spaced from the LCP and communicatively coupled to the LCP, may then initiate a shock therapy program, as shown at 1306. Finally, if the arrhythmia is determined to be susceptible to ATP therapy, LCP 100 may be configured to modify the shock therapy program of the medical device, as shown at 1308.

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

What is claimed is:

1. A medical device system for delivering electrical stimulation therapy to a heart of a patient, the system comprising:
a leadless cardiac pacemaker (LCP) configured to be implanted within a heart of a patient and configured to determine an arrhythmia type of a detected cardiac arrhythmia;
the LCP configured to ascertain if the determined arrhythmia type is susceptible to anti-tachycardia pacing (ATP) therapy;
a medical device configured to deliver defibrillation shock therapy to the patient, wherein the LCP and the medical device are spaced from one another and communicatively coupled, and
wherein:
if the LCP ascertains that the determined arrhythmia type is susceptible to anti-tachycardia pacing (ATP) therapy, the LCP is configured to:
send an instruction to the medical device instructing the medical device to hold off on delivering the defibrillation shock therapy; and
deliver the ATP therapy to the patient's heart; and
if the LCP ascertains that the determined arrhythmia type is not susceptible to anti-tachycardia pacing (ATP) therapy, allow the medical device to deliver the defibrillation shock therapy to the patient without first waiting for the delivery of the ATP therapy by the LCP.

2. The system of claim 1, wherein the LCP determines the arrhythmia type based, at least in part, on one or more physiological signals and/or indications of one or more physiological conditions of the patient.

3. The system of claim 1, wherein the defibrillation shock therapy comprises:
charging a capacitor to a predefined level; and
after charging the capacitor to the predefined level, delivering one or more defibrillation pulses to the heart of the patient using at least some energy stored in the capacitor.

4. The system of claim 3, wherein the instruction sent to the medical device includes a suspend message instructing the medical device to suspend the defibrillation shock therapy at least until after the ATP therapy is delivered by the LCP.

5. The system of claim 4, wherein the suspend message causes the medical device to suspend delivering one or more defibrillation pulses to the heart of the patient after charging the capacitor to the predefined level.

6. The system of claim 4, wherein the suspend message causes the medical device to cease charging the capacitor.

7. The system of claim 4, wherein the LCP is further configured to:
determine whether a delivered ATP therapy terminated the arrhythmia;
if it is determined that the delivered ATP therapy terminated the arrhythmia, communicate an abort command to the medical device instructing the medical device to abort the defibrillation shock therapy;
if it is determined that the delivered ATP therapy failed to terminate the arrhythmia, communicate a resume command to the medical device instructing the medical device to resume the defibrillation shock therapy.

8. The system of claim 7, wherein, after receiving the resume command from the LCP, the medical device is configured to deliver one or more defibrillation pulses to the heart of the patient.

9. The system of claim 1, wherein the medical device is configured to recognize occurrences of a cardiac arrhythmia based, at least in part, on one or more signals received from the LCP.

10. The system of claim 1, wherein the LCP is further configured to:
determine whether the delivered ATP therapy terminated the arrhythmia;
if it is determined that the delivered ATP therapy terminated the arrhythmia, communicate an abort command to the medical device instructing the medical device to abort the defibrillation shock therapy; and
if it is determined that the delivered ATP therapy failed to terminate the arrhythmia, communicate a shock command to the medical device instructing the medical device to resume the defibrillation shock therapy.

11. The system of claim 10, wherein the shock command causes the medical device to deliver one or more defibrillation pulses to the heart of the patient.

12. A method for delivering electrical stimulation therapy to a heart of a patient, the method comprising:
determining an occurrence of an arrhythmia;
after determining an occurrence of an arrhythmia:
with information sensed by a leadless cardiac pacemaker (LCP), determining an arrhythmia type of the arrhythmia;
determining from the arrhythmia type whether the arrhythmia is susceptible to anti-tachycardia pacing (ATP) therapy;
with a medical device that is spaced from the LCP and communicatively coupled to the LCP, initiating a shock therapy program; and
with the LCP, if the arrhythmia is determined to be susceptible to ATP therapy, instructing the medical device to hold off on delivering the shock therapy program of the medical device while the LCP delivers the ATP therapy, and if the arrhythmia is determined not to be susceptible to ATP therapy, allowing the medical device to deliver the shock therapy program without first waiting for the delivery of the ATP therapy by the LCP.

13. The method of claim 12, further comprising determining if the ATP therapy terminated the arrhythmia, and if so, aborting the shock therapy program, and if not, resuming the shock therapy program, wherein the shock therapy program comprises delivering one or more defibrillation pulses to the heart of the patient.

14. The method of claim 12, wherein the arrhythmia is determined to be susceptible to ATP therapy if:
a beat rate of the heart of the patient is less than a threshold beat rate;
a regularity of a beat rhythm of the heart of the patient is greater than a threshold regularity; and/or
the arrhythmia is monomorphic.

15. A medical device system for delivering electrical stimulation therapy to a heart of a patient, the system comprising:

a leadless cardiac pacemaker (LCP) configured to sense one or more physiological parameters of the heart of the patient and to recognize an occurrence of an arrhythmia based at least in part on the one or more sensed parameters;

the LCP further configured to determine an arrhythmia type based at least in part on the one or more sensed physiological parameters of the heart of the patient; and a medical device communicatively coupled to the LCP, the medical device configured to recognize the an occurrence of an arrhythmia and deliver electrical shock therapy to the heart of the patient, wherein the electrical shock therapy comprises:

charging a capacitor to a predetermined level, and delivering one or more electrical shocks to the heart of the patient after charging the capacitor to the predetermined level; and wherein the medical device is configured to alter the electrical shock therapy based on instructions communicated from the LCP in accordance with the determined arrhythmia type.

16. The system of claim 15, wherein the LCP is further configured to, based on the one or more sensed physiological parameters, instruct the medical device to begin charging the capacitor.

17. The system of claim 16, wherein the one or more physiological parameters comprises one or more of:

cardiac electrical activity;
contractility of the heart of the patient;
cardiac output of the heart of the patient; and
heart sounds.

18. The system of claim 16, wherein the LCP instructs the medical device to begin charging the capacitor before the medical device recognizes the occurrence of an arrhythmia.

19. The system of claim 15, wherein the LCP is further configured to:

send a signal including data that can be interpreted by the medical device as indicating the occurrence of the arrhythmia to the medical device, wherein the medical device is further configured to recognize the occurrence of an arrhythmia based, at least in part, on the received signal; and deliver an ATP therapy before the medical device delivers electrical shock therapy to the heart of the patient.

20. The system of claim 19, wherein the LCP is further configured to:

determine whether the ATP therapy was successful in terminating the arrhythmia; and if it is determined that the ATP therapy was successful in terminating the arrhythmia, communicate an abort message to the medical device instructing the medical device to abort the delivery of electrical shock therapy to the heart of the patient.

* * * * *